United States Patent
Xie et al.

(10) Patent No.: US 12,060,416 B2
(45) Date of Patent: *Aug. 13, 2024

(54) HUMANIZED ANTI-VEGF MONOCLONAL ANTIBODY

(71) Applicant: SinoCellTech Ltd., Beijing (CN)

(72) Inventors: Liangzhi Xie, Beijing (CN); Chunyun Sun, Beijing (CN); Rui Wang, Beijing (CN); Xiao Zhang, Beijing (CN)

(73) Assignee: SinoCellTech Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/579,376

(22) Filed: Jan. 19, 2022

(65) Prior Publication Data

US 2022/0144930 A1 May 12, 2022

Related U.S. Application Data

(63) Continuation of application No. PCT/CN2020/102622, filed on Jul. 17, 2020.

(30) Foreign Application Priority Data

Jul. 19, 2019 (CN) .......................... 201910657497.7

(51) Int. Cl.
    *C07K 16/22*     (2006.01)
    *A61K 39/00*     (2006.01)
    *A61K 47/68*     (2017.01)

(52) U.S. Cl.
    CPC .......... *C07K 16/22* (2013.01); *A61K 47/6845* (2017.08); *A61K 2039/505* (2013.01); *C07K 2317/24* (2013.01); *C07K 2317/565* (2013.01); *C07K 2317/567* (2013.01); *C07K 2317/73* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS 10,266,608 B2 * 4/2019 Wu .......................... A61P 25/28

FOREIGN PATENT DOCUMENTS

| CN | 105820244 A | 8/2016 |
|---|---|---|
| CN | 105820245 A | 8/2016 |
| JP | 2007526756 A | 9/2007 |
| JP | 2013502445 A | 1/2013 |
| RU | 2514148 C2 | 4/2014 |
| RU | 2519669 C2 | 6/2014 |
| RU | 2699544 C2 | 9/2019 |
| WO | WO 2911/066503 | * 6/2011 |
| WO | 2017119435 A1 | 7/2017 |

OTHER PUBLICATIONS

An Examiner Requisition issued by the Canadian Intellectual Property Office on Mar. 8, 2022 in connection with corresponding Canadian patent application No. 3,147,921.
International Search Report and Written Opinion dated Oct. 21, 2020 in connection with International Application No. PCT/CN2020/102622, 21 pages.
Kolar, G.R. et al., "Accession No. AAV-40016", Genbank, Jul. 26, 2016, 2 pages.
Kuwata, T., "Accession No. AER46545", Genbank, Jul. 25, 2016, 2 pages.
Goodwin, E. et al., "Accession No. AXA12743", Genbank, Jul. 11, 2018, 2 pages.
Kong, D.H., et al., "A Review of Anit-Angiogenic Targets for Monoclonal Antibody Cancer Therapy", International Journal of Molecular Sciences, Vogust 2017, 25 pages.
A First Office Action issued by China National Intellectual Property Administration on Jun. 13, 2023 in connection with Chinese Patent Application No. 202080046296.4.
A First Office Action issued by Mexican Patent Office on Jun. 7, 2022 in connection with Mexican Patent Application No. MX/a/2022/000779.
A First Office Action issued by the Russian Patent Office on Aug. 18, 2022 in connection with Russian patent Application No. 2022102752.
A First Examination Report issued by the Australian Patent Office on Oct. 13, 2023 in connection with Australian Patent Application No. 2020316498.
An Extended European Search Report issued by the European Patent Office on Oct. 18, 2023 in connection with EPO Patent Application No. 20844414.1.
A First Office Action issued by the Japanese Patent Office on Feb. 13, 2023 in connection with Japanese Patent Application No. 2022-503865.

* cited by examiner

*Primary Examiner* — Marianne P Allen

(57) ABSTRACT

The present invention belongs to the field of tumor immunotherapy, and relates to a humanized monoclonal antibody that binds to VEGF. The present invention discloses nucleic acid sequences (including heavy/light chain variable regions) encoding said antibodies, and vectors, pharmaceutical compositions and kits containing said nucleic acid sequences. The antibody disclosed in the present invention can specifically bind to VEGF with high affinity and block the binding of VEGF to the receptor VEGFR2. Said antibodies also neutralize the proliferative effect of VEGF165 protein and multiple VEGF subtypes on HUVEC cells and can be used in clinical treatment of tumors, including but not limited to: colorectal cancer.

9 Claims, 8 Drawing Sheets

Specification includes a Sequence Listing.

HUMANIZED ANTI-VEGF MONOCLONAL ANTIBODY

CROSS-REFERENCE SECTION

This application is a continuation of and claims priority to PCT Application No. PCT/CN2020/102622 filed Jul. 17, 2020, which itself claims priority to Chinese Patent Application No. 201910657497.7 filed Jul. 19, 2019. The contents from all of the above are hereby incorporated in their entirety by reference.

REFERENCE TO SEQUENCE LISTING SUBMITTED VIA EFS-WEB

This application includes an electronically submitted sequence listing via EFS-Web as an ASCII text file. The ASCII text file contains a sequence listing entitled "10141774-50944164_humanized_anti-vegf_monoclonal_antibody_sequence_listing.txt" created on Jan. 19, 2022 and 78,000 bytes in size. The sequence listing contained in this ASCII text file is part of the specification and is hereby incorporated by reference herein in its entirety.

TECHNICAL FIELD

The present invention relates to the field of tumor immunotherapy, specifically relates to a humanized monoclonal antibody that binds to VEGF.

BACKGROUND

The development of the vascular system is the foundation of many physiological and pathological processes. Vascular endothelial growth factor (VEGF) is a group of growth factors possessing important pro-angiogenic activities that promote endothelial cell mitosis and anti-apoptosis, increase vascular permeability, and promote cell migration. The human VEGF gene is localized on chromosome 6p21.3 and belongs to the VEGF/PDGF supergene family, which encodes VEGF linked by disulfide bonds to form a dimer. In humans, the VEGF family includes multiple members with different functions: VEGFA (VEGF, with several different splicing variants), VEGFB, VEGFC, VEGFD, VEGFE, VEGFF, and placenta growth factor (PIGF). Recently, endocrine gland-derived vascular endothelial growth factor (EG-VEGF) has been also included in this family (Samson M et al., J Clin Endocrinal Metab. 2004; 89(8):4078-4088). VEGF is widely distributed in human tissues and organs, among which the eye retinal pigment epithelial cells, vascular endothelial cells, nerve cells, etc. are expressed (Goel H L et al., Nat Rev Cancer. 2013; 13(12): 871). There are three types of VEGF receptors: VEGFR1, VEGFR2 and VEGFR3. The binding of VEGF to the receptor extracellular domain triggers receptor dimerization and promote autophosphorylation of tyrosine residues in the intracellular domain, thereby activating downstream signals that promote cell proliferation, migration, anti-apoptosis and increased vascular permeability. VEGFR1 and VEGFR2 are mainly expressed in vascular endothelial cells, while VEGFR3 is mainly expressed in lymphatic endothelial cells.

VEGF has been confirmed to play an important role in the regulation of normal and pathological angiogenesis (Melincovici C. S. et al., Rom J Morphol Embryol. 2018; 59(2): 455-467). VEGF is overexpressed in a variety of tumors that can cause malignant ascites, and the expression of VEGF in tumors is correlated with the migration ability of tumor cells. The concentration of VEGF in patients with solid tumors of poorer survival rate such as gastrointestinal, ovarian, breast and lung cancers is positively correlated with disease staging (Sebastian, K et al., Oncologist. 2009; 14(12): 1242-1251). Hypoxic conditions in the tumor microenvironment induce the entry of tumor cell transcription factor HIF-1a into the nucleus, sequentially HIF-1a bind to the HRE element of VEGFA, thereby the transcription level of VEGFA is up-regulated and tumor cells is promoted to secrete large amounts of VEGF into the tumor microenvironment. In turn, the high concentration of VEGF acts on VEGFRs on vascular endothelial cells, inducing a large number of neovascularization, enhancing blood supply, and providing sufficient nutrients for the growth of tumor cells. More VEGF is secreted from the rapid-grown tumor cells, which further promotes the proliferation and migration of vascular endothelial cells and induces tumor metastasis. In addition, VEGF also stimulates monocytes in tumor tissues to convert to M2 suppressor macrophages, producing more negative immune factors, and up-regulating Treg cells at the same time, which synergistically reduce the killing ability of T cells.

By inhibiting the interaction of VEGF with endothelial cell surface receptors VEGFR2 and VEGFR1, VEGF monoclonal antibody drugs block downstream signaling pathways, inhibit endothelial cell proliferation and neovascularization, deprive tumor tissues of blood supply, and control the internal nutrient supply of tumors, thereby limiting tumor growth and ultimately achieving anticancer efficacy. Avastin (bevacizumab, approved in 2009) is the first antibody drug approved to inhibit tumor angiogenesis, and is mainly used for the treatment of breast cancer, cervical cancer, colorectal cancer, glioblastoma, glioma, non-small cell lung cancer, ovarian cancer, and renal cell carcinoma. Although Avastin has been used to treat a variety of cancers, there is still a need in the field for more potent antibodies with greater VEGF inhibition and higher efficacy.

The present invention provides a novel human VEGF antibody for the treatment of colorectal cancer.

SUMMARY

In one aspect, the present invention provides an isolated anti-VEGF antibody or antigen-binding fragment thereof, comprising a heavy chain variable region having a heavy chain CDR1 region having the amino acid sequence as set forth in SEQ ID NO: 30, a heavy chain CDR2 region having the amino acid sequence as set forth in SEQ ID NO: 31 and a heavy chain CDR3 region having the amino acid sequence as set forth in SEQ ID NO: 32; and a light chain variable region having a light chain CDR1 region having the amino acid sequence as set forth in SEQ ID NO: 27, a light chain CDR2 region having the amino acid sequence as set forth in SEQ ID NO: 28, and a light chain CDR3 region having the amino acid sequence as set forth in SEQ ID NO: 29.

In one embodiment, said anti-VEGF antibody or antigen-binding fragment thereof has a heavy chain variable region having the amino acid sequence as set forth in SEQ ID NO: 39, or the amino acid sequences having at least 90%, 92%, 95%, 98% or 99% sequence identity to SEQ ID NO: 39; and a light chain variable region having the amino acid sequence as set forth in SEQ ID NO: 40, or the amino acid sequences having at least 90%, 92%, 95%, 98% or 99% sequence identity to SEQ ID NO: 40.

In one embodiment, said antibody further comprises a light chain constant region and a heavy chain constant region, preferably the light chain constant region is the light chain constant region having the amino acid sequence as set forth in SEQ ID NO: 42, or the amino acid sequences having at least 90%, 92%, 95%, 98%, or 99% sequence identity to SEQ ID NO: 42; and/or the heavy chain constant region is the IgG1 heavy chain constant region having the amino acid sequence as set forth in SEQ ID NO: 41, or the amino acid sequences having at least 90%, 92%, 95%, 98%, or 99% sequence identity to SEQ ID NO: 41.

In one embodiment, said anti-VEGF antibody or antigen-binding fragment thereof is an IgG antibody, preferably an IgG1 antibody.

In one embodiment, said anti-VEGFR antibody or antigen-binding fragment thereof is a monoclonal antibody.

In one embodiment, the binding affinity $K_D$ of said anti-VEGF antibody or antigen-binding fragment thereof to the recombinant human VEGF165 protein is 1-100 μM, preferably 5-50 μM, and more preferably 19.5 μM.

In one embodiment, said antigen-binding fragment is Fv, Fab, Fab', Fab'-SH, F(ab')2, Fd fragment, Fd' fragment, single chain antibody molecule or single domain antibody; wherein the single chain antibody molecule is preferably scFv, di-scFv, tri-scFv, diabody or scFab.

In another aspect, the present invention provides an antibody-drug conjugate, comprising the anti-VEGF antibody or antigen-binding fragment thereof as described herein and an additional therapeutic agent, preferably said anti-VEGF antibody or antigen-binding fragment thereof is connected with the additional therapeutic agent via a connector.

In one aspect, the present invention provides an isolated anti-VEGF antibody or antigen-binding fragment thereof, comprising a heavy chain variable region having a heavy chain CDR1 region having the amino acid sequence as set forth in SEQ ID NO: 16 and a heavy chain CDR2 region having the amino acid sequence as set forth in SEQ ID NO: 17 and a heavy chain CDR3 region having the amino acid sequence as set forth in SEQ ID NO: 18; and a light chain variable region having a light chain CDR1 region having the amino acid sequence as set forth in SEQ ID NO: 13, a light chain CDR2 region having the amino acid sequence as set forth in SEQ ID NO: 14, and a light chain CDR3 region having the amino acid sequence as set forth in SEQ ID NO: 15.

In one embodiment, said anti-VEGF antibody or antigen-binding fragment thereof comprises a heavy chain constant region having the amino acid sequence as set forth in SEQ ID NO: 25, or the amino acid sequences having at least 90%, 92%, 95%, 98%, or 99% sequence identity to SEQ ID NO: 25; and a light chain variable region having the amino acid sequence as set forth in SEQ ID NO: 26, or the amino acid sequences having at least 90%, 92%, 95%, 98%, or 99% sequence identity to SEQ ID NO: 26.

In one embodiment, said anti-VEGF antibody or antigen-binding fragment thereof is a humanized antibody or a chimeric antibody.

In another aspect, the present invention provides a nucleic acid encoding the anti-VEGF antibody or antigen-binding fragment thereof as described herein.

In one embodiment, said nucleic acid comprises the nucleotide sequence as set forth in SEQ ID NO: 7 and/or the nucleotide sequence as set forth in SEQ ID NO: 8; or comprises the nucleotide sequence as set forth in SEQ ID NO: 23 and/or the nucleotide sequence as set forth in SEQ ID NO: 24; or comprises the nucleotide sequence as set forth in SEQ ID NO: 47 and/or the nucleotide sequence as set forth in SEQ ID NO: 48.

In another aspect, the present invention provides an expression vector, comprising the nucleic acid as described herein.

In another aspect, the present invention provides a host cell, comprising the nucleic acid as described herein or the expression vector as described herein.

In another aspect, the present invention provides a method for producing the anti-VEGF antibody or antigen-binding fragment thereof as described herein, comprising culturing the host cell as described herein under conditions suitable for antibody expression, and harvesting the expressed antibody from the culture medium.

In another aspect, the present invention provides a pharmaceutical composition, comprising the anti-VEGF antibody or antigen-binding fragment thereof as described herein, or the antibody-drug conjugate as described herein, or the nucleic acid as described herein, or the expression vector as described herein, and a pharmaceutically acceptable carrier.

In one embodiment, the present invention provides the anti-VEGF antibody or antigen-binding fragment thereof as described herein, or the antibody-drug conjugate as described herein, or the pharmaceutical composition as described herein, for use in the treatment of colorectal cancer.

In another aspect, the present invention provides a method for treating colorectal cancer, comprising administering to a subject in need a therapeutically effective amount of the anti-VEGF antibody or antigen-binding fragment thereof as described herein, or the antibody-drug conjugate as described herein, or the pharmaceutical composition as described herein.

In another aspect, the present invention provides the use of the anti-VEGF antibody or antigen-binding fragment thereof as described herein or the antibody-drug conjugate as described herein or the pharmaceutical composition as described herein in the preparation of a medicament for the treatment of colorectal cancer.

In another aspect, the present invention provides a pharmaceutical combination, comprising the anti-VEGFR2 antibody or antigen-binding fragment thereof as described herein, or the antibody-drug conjugate as described herein, or the pharmaceutical composition as described herein, and one or more additional therapeutic agents.

In another aspect, the present invention provides a kit, comprising the anti-VEGF antibody or antigen-binding fragment as described herein, or the antibody-drug conjugate as described herein, or the pharmaceutical composition as described herein, preferably, further comprising a device for administration.

BRIEF DESCRIPTION OF THE DRAWINGS

The present invention is illustrated in combination with the attached drawings, in which.

DETAILED DESCRIPTION

Figure 1:
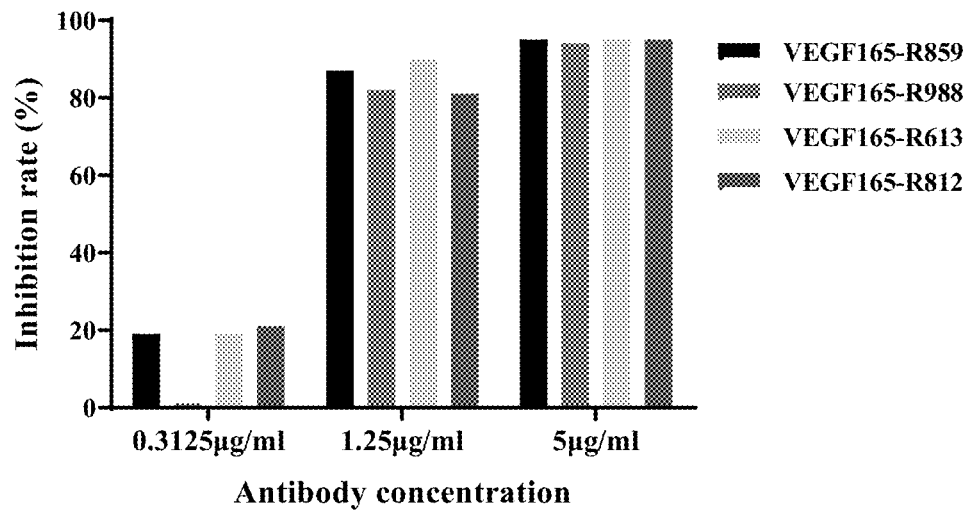
FIG. 1 shows that the rabbit antibody VEGF165 blocks the binding of VEGF165 to VEGFR2 protein.

Various aspects of the present invention relate to an isolated anti-VEGF antibody or antigen-binding fragment thereof, an antibody-drug conjugate comprising said antibody or antigen-binding fragment thereof, a nucleic acid and an expression vector encoding said antibody or antigen-binding fragment thereof, and a host cell containing said nucleic acid or expression vector, a method for producing said anti-VEGF antibody or antigen-binding fragment thereof, a pharmaceutical composition comprising said anti-VEGF antibody or antigen-binding fragment thereof, and a method of using said anti-VEGF antibody or antigen-binding fragment thereof for treating colorectal cancer.

Definition

Unless otherwise stated, all technical and scientific terms used herein have the meaning normally understood by a person skilled in the art to which the present invention belongs. For the purposes of the present invention, the following terms are defined to be consistent with the meanings commonly understood in the art.

When used herein and in the appended claims, the singular forms "one", "a/an", "another" and "said" include the plural designation of the object unless the context clearly indicates otherwise.

The term "antibody" refers to an immunoglobulin molecule and refers to any form of antibody that exhibits the desired biological activity. These include, but are not limited to, monoclonal antibodies (including full-length monoclonal antibodies), polyclonal antibodies and multispecific antibodies (e.g. bispecific antibodies), and even antibody fragments. Typically, full-length antibody structures preferably comprise four polypeptide chains, two heavy (H) chains and two light (L) chains, typically interconnected by disulfide bonds. Each heavy chain contains a heavy chain variable region and a heavy chain constant region. Each light chain contains a light chain variable region and a light chain constant region. In addition to this typical full-length antibody structure, the structure also includes other derivative forms.

Said heavy chain variable region and light chain variable region can be further subdivided into more conservative regions (called framework regions (FR)) and hypervariable regions (called complementarity determining regions (CDR)) interspersed therewith.

The term "complementary determining region" (CDR, e.g. CDR1, CDR2 and CDR3) refers to such amino acid residues in the variable region of an antibody whose presence is necessary for antigen binding. Each variable region typically has three CDR regions identified as CDR1, CDR2 and CDR3. Each complementary determining region may contain amino acid residues from a "complementary determining region" as defined by Kabat (Kabat et al., Sequences of Proteins of Immunological Interest, 5th Ed. Public Health Service, National Institutes of Health, Bethesda, MD. 1991) and/or those residues from the "high-variable loop" (Chothia and Lesk; J MolBiol 196: 901-917 (1987)).

The term "framework" or "FR" residues are those residues within the variable region other than CDR residues as defined herein.

Each heavy chain variable region and light chain variable region typically contains 3 CDRs and up to 4 FRs, said CDRs and FRs being arranged from the amino terminus to the carboxyl terminus in the following order, for example: FR1, CDR1, FR2, CDR2, FR3, CDR3, and FR4.

The complementary determining region (CDR) and the framework region (FR) of a given antibody can be identified using the Kabat system (Kabat et al: Sequences of Proteins of Immunological Interest, 5th edition, US Department of Health and Human Services, PHS, NIH, NIH Publication No. 91-3242, 1991).

The term "constant region" refers to such amino acid sequences in the light and heavy chains of an antibody that are not directly involved in the binding of the antibody to the antigen but exhibit a variety of effector functions such as antibody-dependent cytotoxicity.

According to the antigenic differences of the amino acid sequence of its constant region, the heavy chain of an antibody can be classified into five classes: a, δ, ε, γ, and u. When it forms a complete antibody with the light chain, it can be classified into five classes: IgA, IgD, IgE, IgG and IgM, of which can be further classified into subclasses (isotypes), such as IgG1, IgG2, IgG3, IgG4, IgA and IgA2. Based on the amino acid sequence of its constant domain, the light chain of an antibody can be classified into k and λ.

An "antigen-binding fragment of an antibody" comprises a portion of an intact antibody molecule that retains at least some of the binding specificity of the parent antibody and typically includes at least a portion of the antigen-binding region or variable region (e.g. one or more CDRs) of the parent antibody. Examples of antigen-binding fragments include, but are not limited to, Fv, Fab, Fab', Fab'-SH, F(ab')2, Fd fragment, Fd' fragment, single chain antibody molecules (e.g. scFv, di-scFv or tri-scFv, diabody or scFab), single domain antibodies.

The term "antibody fragment" refers to a non-intact antibody molecule that retains at least some of the biological properties of the parent antibody, including, but not limited to, an Fc fragment, in addition to those described above as "antigen-binding fragments".

The term "antibody-drug conjugate" or "ADC" refers to a binding protein, such as an antibody or antigen-binding fragment thereof, that chemically linked to one or more of chemical drugs (also referred to as agents herein), which may optionally be a therapeutic agent or a cytotoxic agent. In a preferred embodiment, an ADC includes an antibody, a cytotoxic or therapeutic drug, and a linker that enables the drug to be linked or conjugated to the antibody. ADCs usually have any value of 1 to 8 drugs conjugated to the antibody, including 2, 4, 6, or 8 drug-loading substances. Non-limiting examples of drugs that can be included in the ADCs are mitotic inhibitors, anti-tumor antibiotics, immunomodulators, vectors for gene therapy, alkylating agents, anti-angiogenic agents, antimetabolites, boron-containing agents, chemotherapeutic protective agents, hormones, anti-hormonal agents, corticosteroids, photoactive therapeutic agents, oligonucleotides, radionuclide agents, topoisomerase inhibitors, tyrosine kinase inhibitors and radiosensitizers.

The term "chimeric antibody" refers to an antibody in which a part of the heavy chain and/or light chain is derived from a specific source or species, and the remaining part is derived from a different source or species. The "chimeric antibody" may also be a functional fragment as defined above. "Humanized antibodies" are a subset of "chimeric antibodies."

The term "humanized antibody" or "humanized antigen-binding fragment" is defined herein as an antibody or antibody fragment that is: (i) derived from a non-human source (e.g., a transgenic mouse carrying a heterologous immune system) and based on a human germline sequence; or (ii) a chimeric antibody where the variable region is of non-human origin and the constant region is of human origin; or (iii) a CDR transplant where the CDR of the variable region is of non-human origin and one or more frame work regions of the variable region are of human origin and the constant region, if any, is of human origin. The aim of "humanization" is to eliminate the immunogenicity of antibodies of non-human origin in the human body, while retaining the greatest possible affinity. It is advantageous to select the human framework sequence that is most similar to the framework sequence of the non-human source antibody as the template for humanization. In some cases, it may be necessary to replace one or more amino acids in the human framework sequence with corresponding residues in the non-human construct to avoid loss of affinity.

The term "monoclonal antibody" refers to an antibody derived from a substantially homogeneous population of antibodies, i.e. every single antibody comprised in the population is identical except for possible mutations (e.g. natural mutations) which may be present in very small quantities. The term "monoclonal" therefore indicates the nature of the antibody in question, i.e. not a mixture of unrelated antibodies. In contrast to polyclonal antibody preparations, which usually comprise different antibodies against different epitopes, each monoclonal antibody in a monoclonal antibody preparation is directed against a single epitope on the antigen. In addition to their specificity, monoclonal antibody preparations have the advantage that they are usually not contaminated by other antibodies. The term "monoclonal" should not be understood as requiring the production of said antibodies by any particular method.

The antibody "specifically binds" to a target antigen such as a tumor-associated peptide antigen target (in this case, PD-1), i.e. binds said antigen with sufficient affinity to enable said antibody to be used as a therapeutic agent, targeting a cell or tissue expressing said antigen, and does not significantly cross-react with other proteins, or does not significantly cross-react with proteins other than the homologues and variants of the target proteins mentioned above (e.g. mutant forms, splice variants, or protein hydrolysis truncated forms).

The term "binding affinity" refers to the strength of the sum of the non-covalent interactions between a molecule's individual binding sites and its binding partners. Unless otherwise stated, "binding affinity", when used herein, refers to the intrinsic binding affinity, which reflects a 1:1 interaction between members of a binding pair (e.g. antibody and antigen). As used herein, the term "$K_D$" refers to the equilibrium dissociation constant of the antibody-antigen interaction. As used herein, the term "$k_{on}$" refers to the rate constant at which an antibody binds to an antigen. As used herein, the term "$k_{off}$" refers to the rate constant at which an antibody dissociates from an antibody/antigen complex. "$K_D$", "binding rate constant $k_{on}$" and "dissociation rate constant $k_{off}$" are commonly used to describe the affinity between a molecule (e.g. an antibody) and its binding partner (e.g. an antigen). Affinity, i.e. the tight degree at which a ligand binds a particular protein. Binding affinity is influenced by non-covalent intermolecular interactions such as hydrogen bonding, electrostatic interactions, hydrophobic and van der Waals forces between two molecules. In addition, the binding affinity between a ligand and its target molecule may be influenced by the presence of other molecules. Affinity can be analyzed by conventional methods known in the art, including the ELISA described herein.

The term "epitope" includes any protein determinant cluster that specifically binds to an antibody or T-cell receptor. Epitope determinant clusters typically consist of a molecule's chemically active surface groups (e.g. amino acid or sugar side chains, or a combination thereof) and often have specific three-dimensional structural features as well as specific charge characteristics.

The term "isolated" antibody is an antibody that has been identified and isolated from the components of the cell where the antibody expressed. Isolated antibodies include in situ antibodies inside of recombinant cells, where at least one component in natural environment of said antibody is absent. However, usually, the isolated antibody is prepared through at least one purification step.

"sequence identity" between two polypeptides or nucleic acid sequences indicates the number of residues that are identical between said sequences as a percentage of the total number of residues, and is calculated based on the size of the smaller of the compared molecules. When calculating the percentage identity, the sequences being aligned are matched in such a way as to produce a maximum match between the sequences, with the gaps in the match (if present) being resolved by a specific algorithm. Preferred computer program methods for determining identity between two sequences include, but are not limited to, GCG program packages including GAP, BLASTP, BLASTN and FASTA (Altschul et al., 1990, J. Mol. Biol. 215: 403-410).

The above procedures are publicly available from the International Center for Biotechnology Information (NCBI) and other sources. The well-known Smith Waterman algorithm can also be used to determine identity.

The term "Fc receptor" or "FcR" refers to a receptor that binds to the Fc region of an antibody. Human FcRs of natural sequence are preferred, and preferably receptors that bind to IgG antibodies (gamma receptors), which include the FcγRI, FcγRII and FcγRIII isoforms, as well as variants of these receptors. All other FcRs are included in the term "FcR". The term also includes the neonatal receptor (FcRn), which is responsible for the transport of maternal IgG to the fetus (Guyer et al, Journal of Immunology 117: 587 (1976) and Kim et al, Journal of Immunology 24: 249 (1994)).

The term "neonatal Fc receptor", abbreviated as "FcRn", binds to the Fc region of IgG antibodies. The neonatal Fc receptor (FcRn) plays an important role in the metabolic fate of IgG-like antibodies in vivo. FcRn functions to rescue IgG from the lysosomal degradation pathway, thereby reducing its clearance in serum and lengthening its half-life. Therefore, the in vitro FcRn binding properties/characteristics of IgG are indicative of its in vivo pharmacokinetic properties in the circulation.

The term "effector function" refers to those biological activities attributable to the Fc region of an antibody, which vary from isotype to isotype. Examples of antibody effector functions include C1q binding and complement-dependent cytotoxicity (CDC), Fc receptor binding, antibody-dependent cell-mediated cytotoxicity (ADCC), antibody-dependent cellular phagocytosis (ADCP), cytokine secretion, immune complex-mediated uptake of antigen by antigen-presenting cells, cell surface receptors down-regulation (e.g. B-cell receptors) and B-cell activation.

The term "effector cell" refers to a cell that expresses one or more FcRs and performs effector functions. In one aspect, said effector cells express at least FcγRIII and perform ADCC effector functions. Examples of human cells that mediate ADCC include peripheral blood mononuclear cells (PBMCs), natural killer (NK) cells, monocytes, cytotoxic T cells and neutrophils. Effector cells can be isolated from natural sources, for example, blood. Effector cells are usually lymphocytes associated with effector phase and function to produce cytokines (helper T cells), kill cells infected by pathogens (cytotoxic T cells) or secrete antibodies (differentiated B cells).

"Immune cells" include cells that have a haematopoietic origin and play a role in the immune response. Immune cells include lymphocytes, such as B cells and T cells; natural killer cells; and myeloid cells, such as monocytes, macrophages, eosinophils, mast cells, basophils and granulocytes.

"Antibody-dependent cell-mediated cytotoxicity" or "ADCC" refers to a form of cytotoxicity in which secreted Ig binds to Fcγ receptors presented on certain cytotoxic cells (e.g. NK cells, neutrophils and macrophages) allows these cytotoxic effector cells to specifically bind to target cells bearing antigens and subsequently kill said target cells using, for example, a cytotoxin. To assess the ADCC activity of the target antibody, in vitro ADCC assays can be performed, such as the in vitro ADCC assays documented in U.S. Pat. No. 5,500,362 or 5,821,337 or U.S. Pat. No. 6,737,056 (Presta). Useful effector cells for use in such assays include PBMCs and NK cells.

"Complement-dependent cytotoxicity" or "CDC" refers to the lysis of target cells in the presence of complement. The classic pathway for complement activation is initiated by binding the first component of the complement system (C1q) to an antibody (of the appropriate subclass) that binds to its corresponding antigen. To assess complement activation, a CDC assay can be performed, such as the CDC assay recited in Gazzano-Santoro et al., J. Immunol Methods 202: 163 (1996). For example in U.S. Pat. No. 6,194,551 B1 and WO1999/51642, there described polypeptide variants having altered amino acid sequences of the Fc region (polypeptides having a variant Fc region) and polypeptide variants having enhanced or reduced C1q binding.

Amino Acid Sequence and Nucleotide Sequence of the Antibody of the Present Invention The present invention used recombinant human VEGF165 protein to immunize rabbit, and then obtained the antibody clones VEGF-R859, VEGF-R988, VEGF-R613 and VEGF-R812 that specifically bind to recombinant human VEGF165 protein by phage display library screening. The nucleotide sequence encoding the heavy and light chain variable regions of the VEGFR2-MK19 scFv antibody was then inserted by PCR into pSTEP2 vector harboring nucleotide sequence encoding the rabbit IgG1 constant region or the rabbit kappa constant region, and cultured for expression. The high purity antibodies were purified using a protein A purification column. ELISA showed that said rabbit antibody was able to block the binding of VEGF165 protein to VEGFR2 protein, and VEGF-R988 and VEGF-R613 could effectively reduce the ability of VEGF165 to promote HUVEC proliferation, and VEGF-R988 showed a higher maximum inhibition rate.

Then, using the classic method for humanized CDR transplantation, the human antibody light chain or heavy chain variable region whose sequence is closer to the sequence of rabbit light chain or heavy chain variable region was elected as the template, the humanized light chain variable region (VL) and heavy chain variable region (VH) sequences were obtained by inserting each of the three CDRs (Table 1) of the rabbit antibody light chain or heavy chain into the variable regions of said human antibody. As the key sites of the rabbit framework region are essential for maintaining the stability of the CDR activity, the key sites were reverse-mutated to the corresponding sequence of rabbit antibody. VEGF-H988-10 light chain/heavy chain expression vector was obtained by whole gene synthesis, transfected into HEK-293 cells and cultured for expression, and the culture supernatant was purified using a protein A purification column to obtain high purity antibodies. To improve the affinity of VEGF-H988-10, SDM libraries of CDR regions of heavy and light chain variable regions (including LCDR1, LCDR3, HCDR2 and HCDR3) were constructed, and the four mutant libraries were constructed in scFv form and were cloned into phage vectors as svFv-gIII fusion protein; for each CDR, the CDR clones having optimal binding ability to soluble antigen VEGF were screened, and finally the antibody VEGF-H988 having optimized CDR affinity and stability was obtained.

Nucleic Acids of the Present Invention

The present invention also relates to nucleic acid molecules encoding antibodies or portions thereof of the present invention. The sequences of these nucleic acid molecules include, but are not limited to, SEQ ID NOs: 11, 19-20, 23-24, 43-51 and 53-54.

The nucleic acid molecules of the present invention are not limited to the sequences disclosed herein, but also include variants thereof. Variants in the present invention may be described with reference to their physical properties in hybridization. It will be recognized by those of skill in the art that using nucleic acid hybridization techniques, nucleic acids can be used to identify their complements as well as their equivalents or homologues. It will also be recognized that hybridization can occur at less than 100% complementarity. However, given the appropriate choice of conditions, hybridization techniques can be used to distinguish said DNA sequences based on the structural relevance of the DNA sequence to a particular probe. For guidance on such conditions, see Sambrook et al., Molecular Cloning: A Laboratory Manual, 2nd Ed. Cold Spring Harbor Press, Cold Spring Harbor, N. Y., 1989 and Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons.

Recombinant Vectors and Expression

The present invention also provides recombinant constructs comprising one or more nucleotide sequences of the present invention. The recombinant construct of the present invention is constructed by inserting the nucleic acid molecule encoding the antibody of the present invention into a vector such as a plasmid, phagemid, phage or viral vector.

The antibodies provided herein can be prepared by recombinantly expressing nucleotide sequences encoding light and heavy chains or portions thereof in a host cell. In order to recombinantly express the antibody, the host cell may be transfected with one or more recombinant expression vectors carrying nucleotide sequences encoding the light and/or heavy chains or portions thereof, so that said light and heavy chains are expressed in said host cell. Standard recombinant DNA methodologies are used to prepare and/or obtain nucleic acids encoding heavy and light chains, to incorporate these nucleic acids into recombinant expression vectors and to introduce said vectors into host cells, e.g. Sambrook, Fritsch and Maniatis (eds.), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and those documented in U.S. Pat. No. 4,816,397 by Boss et al.

Suitable host cells are prokaryotic and eukaryotic cells. Examples of prokaryotic host cells are bacteria and examples of eukaryotic host cells are yeast, insect or mammalian cells. It should be understood that the design of an expression vector including the selection of a regulatory sequence is determined by a number of factors, such as the choice of host cell, the level of expression of the desired protein and whether the expression is constitutive or inducible.

Bacterial Expression

By inserting a structural DNA sequence encoding the desired antibody together with appropriate translation initiation and termination signals and functional promoters into an operable reading frame, an expression vector for use in bacteria is constructed. The vector will contain one or more phenotypic selection markers and an origin of replication to ensure the maintenance of the vector and provide amplification in the host as needed. Suitable prokaryotic hosts for transformation include multiple species of *E. coli, Bacillus subtilis, Salmonella typhimurium*, as well as *Pseudomonas, Streptomyces* and *Staphylococcus*.

The bacterial vector may be, for example, phage-, plasmid- or phagemid-based. These vectors may contain selection markers and bacterial replication origins, which are derived from commercially available plasmids that usually contain elements of the well-known cloning vector pBR322 (ATCC 37017). After transforming an appropriate host strain and growing the host strain to an appropriate cell density, the selected promoter is de-repressed/induced by an appropriate method (for example, temperature change or chemical induction), and the cells are cultured for an additional time. The cells are usually harvested by centrifugation, disrupted by physical or chemical methods, and the resulting crude extract is retained for further purification.

In a bacterial system, a variety of expression vectors can be advantageously selected according to the intended use of the expressed protein. For example, when a large number of such proteins are to be produced for antibody production or for peptide library screening, for example, a vector that directs high-level expression of a fusion protein product to be easily purified may be required.

Mammalian Expression and Purification

Preferred regulatory sequences for expression in mammalian host cells include viral elements that direct high-level protein expression in mammalian cells, such as promoters and/or enhancers derived from cytomegalovirus (CMV) (e.g., CMV promoter/enhancer), promoters and/or enhancers of simian virus 40 (SV40) (e.g. SV40 promoter/enhancer), promoters and/or enhancers of adenovirus (e.g. adenovirus major late promoter (AdMLP)) and promoters and/or enhancers of polyoma virus. For a further description of viral regulatory elements and their sequences, see, for example, U.S. Pat. No. 5,168,062 by Stinski, U.S. Pat. No. 4,510,245 by Bell et al., and U.S. Pat. No. 4,968,615 by Schaffner et al. The recombinant expression vector may also include an origin of replication and a selection marker (see, for example, U.S. Pat. Nos. 4,399,216, 4,634,665 and 5,179,017 by Axel et al). Suitable selection markers include genes that confer resistance to drugs such as G418, hygromycin, or methotrexate to host cells into which the vector has been introduced. For example, the dihydrofolate reductase (DHFR) gene confers resistance to methotrexate, while the neo gene confers resistance to G418.

The transfection of the expression vector into host cells can be performed using standard techniques such as electroporation, calcium phosphate precipitation, and DEAE-dextran transfection.

Suitable mammalian host cells for expressing the antibodies provided herein include Chinese Hamster Ovary (CHO cells) [including dhfr-CHO cells, as described in Urlaub and Chasin, (1980) Proc. Natl. Acad. Sci. USA 77:4216-4220, DHFR selection markers are employed, as described in, for example, R. J. Kaufman and P. A. Sharp (1982) Mol. Biol. 159:601-621], NSO myeloma cells, COS cells, and SP2 cells.

The antibodies of the present invention can be recovered and purified from recombinant cell culture by known methods, including but not limited to, ammonium sulfate or ethanol precipitation, acid extraction, protein A affinity chromatography, protein G affinity chromatography, anion or cation exchange chromatography, phosphocellulose chromatography, hydrophobic interaction chromatography, affinity chromatography, hydroxyapatite chromatography, and lectin chromatography. High performance liquid chromatography ("HPLC") can be used for purification as well. See, for example, Colligan, Current Protocols in Immunology, or Current Protocols in Protein Science, John Wiley & Sons, NY, N.Y., (1997-2001), for example, Chapters 1, 4, 6, 8, 9, and 10, each of which is incorporated herein by reference in its entirety.

Characteristics and Functions of the Antibodies of the Present Invention

Characteristic analysis and function analysis of the humanized antibody VEGF-H988 of the present invention were performed. The analyses showed that the antibody of the present invention has the following advantages: (1) The ability of VEGF-H988 to bind VEGF165 protein is slightly better than that of Avastin; (2) The binding affinity of VEGF165-H988 to recombinant human VEGF165 protein is slightly higher than that of Avastin, which is about 1.5 times that of Avastin; (3) VEGF165-H988 specifically binds to recombinant human VEGF165 protein and cross-binds to recombinant mouse mVEGF164 protein; (4) antibody VEGF-H988 can effectively inhibit the binding of VEGFR2 protein to VEGF165 protein, and its inhibitory ability is weaker than EYLEA but better than Avastin; (5) antibody VEGF-H988 can effectively reduce the ability of VEGF165 to promote HUVEC proliferation; (6) antibody VEGF-H988 has a stronger neutralizing effect than Avastin in the case of different isoforms of VEGF (VEGF165, VEGFC, VEGFD) acting simultaneously on HUVEC cells; (7) Repeated drug administration toxicity testing in mice showed that no significant drug-related toxic reactions were observed with antibody VEGF-H988; and (8) Tumor suppression test of HCT-116 xenograft tumor model showed that VEGF-H988 has a better effect on tumor inhibition than Avastin.

Uses

The antibodies of the present invention can be used to treat colorectal cancer. The antibody of the present invention can also be used to prepare medicines for the treatment of said disorders.

Pharmaceutical Compositions

Antibodies of the present invention may be prepared with at least one other agent (e.g. a stable compound) to form pharmaceutical compositions comprising an antibody of the present invention and one or more pharmaceutically acceptable carriers, diluents or excipients. Optionally, the pharmaceutical compositions may contain additional therapeutic agents.

Kits

The present invention also relates to a pharmaceutical package and a kit comprising one or more containers, said containers contains the foregoing pharmaceutical compositions of the present invention. Accompanied with such containers may be specifications in the form prescribed by the governmental agency governing the manufacture, use or distribution of the drug or biological product, which reflect approval for human administration by the agency in which said product is manufactured, used or distributed.

Preparation and Storage

The pharmaceutical compositions of the present invention can be prepared in a manner known in the art, for example by conventional mixing, dissolution, granulation, pastille preparation, grinding, emulsification, encapsulation, embedding or lyophilization methods.

Having already prepared pharmaceutical compositions comprising compounds of the present invention formulated in an acceptable carrier, they may be placed in appropriate containers and labeled for the treatment of the condition indicated. Such labeling would include the amount, frequency and administration routes of the drug.

Combinations

The pharmaceutical compositions comprising the antibodies of the present invention described above are also combined with one or more other therapeutic agents, such as antineoplastic agents, wherein the resulting combination does not cause unacceptable adverse effects. The following examples facilitate a better understanding of the present invention, but do not intend to limit the present invention. The experimental methods in the following examples, unless otherwise specified, are all conventional methods. The experimental materials used in the following examples, unless otherwise specified, were purchased from conventional biochemical reagent distributors.

Examples

Example 1: Screening of Rabbit Antibodies that Block the Binding of VEGF165 to VEGFR1/VEGFR2 Using Antibody Phage Display Library 1.1 Immunization of Rabbits Recombinant human VEGF165 protein (from Sino Biological, Inc, Cat. 11066-HNAH) was used to immunize rabbits. The amino acid sequence of the extracellular region Met1-Arg191 of the human VEGF165 protein (UniProt P15692-4) is SEQ ID NO: 1.

The detailed method was: the recombinant human VEGF165 protein was mixed with Freund's adjuvant, the rabbits were subcutaneously immunized with the mixture for 4 times at intervals of 3 weeks, 2 weeks and 2 weeks respectively, at a dose of 500 μg each time. Since the fourth immunization, blood was collected 4 days after immunization via the medial canthal plexus of the eye. The serum titer of rabbit anti-VEGF165 was measured by ELISA using coated recombinant human VEGF165 protein. The titer of the serum from the fifth immunization reached 1:250000, and the rabbits were boosted intravenously with 25 μg recombinant human VEGF165 protein 9 weeks after the fifth immunization. 7 days later, the mice were executed and the spleen tissue was removed and frozen in liquid nitrogen.

1.2 Screening of Antibody Phage-Display Library

RNA was extracted from rabbit spleen tissue using TriPure Isolation Reagent (from Roche, Cat. No. 11 667 165 001), and cDNAs were obtained by reverse transcription of RNA using a reverse transcription kit (from Invitrogen Cat. No. 18080-051). 10 pairs of primers were designed to amplify the sequence of the light chain variable region of the rabbit antibody and 4 pairs of primers were designed to amplify the sequence of the heavy chain variable region (Barbas C F et al., CSHL Press. 2004). The sequences encoding the light and heavy chain variable regions of the rabbit antibody were assembled into the nucleotide sequence encoding scFv by overlapping extension PCR, the light and heavy chain variable regions were linked (Jones S T et al., Bio/technology. 1991; 9(1): 88) by the following linker:

(SEQ ID NO: 2)
TCTAGTGGTGGCGGTGGTTCGGGCGGTGGTGGAGGTGGTAGTTCTAGAT
CTTCC (SSGGGGSGGGGGSSRSS) (corresponding to the
amino acid sequence of SEQ ID NO: 52);

Then enzymatically ligated into the phage vector pComb3× (from Sino Biological, Inc.) by restriction endonuclease Sfi I (from Fermentas), and was electrotransformed into the competent X-Blue to construct the rabbit phage-display scFv antibody library. The recombinant human VEGF165 protein was coated on an ELISA plate, and a phage library enriched with anti-VEGF165 positive antibodies was screened according to the process of phage antibody panning process (O'Brien, P M, & Aitken, R. (Eds.), Springer Science & Business Media. 2002; ISBN: 9780896037113). Single colony phages were selected from the enriched library for expression, and their binding to recombinant human VEGF165 protein was detected by ELISA. The scFv antibody clones that specifically bind to recombinant human VEGF165 were selected and were sent to a sequencing service company for sequencing to obtain the nucleotide sequences of the antibodies, wherein several scFv antibody clones were derived into VEGF-R859 (SEQ ID NO: 3), VEGF-R988 (SEQ ID NO: 4) (the corresponding amino acid sequence being SEQ ID NO: 51), VEGF-R613 (SEQ ID NO: 5), VEGF-R812 (SEQ ID: 6) by the method described in Example 1.3. The nucleotide sequences of their scFV antibody clones are SEQ ID NO: 3. SEQ ID NO: 4, SEQ ID NO: 5, and SEQ ID NO: 6.

1.3 Production of Rabbit Antibodies Targeting VEGF165

Taking VEGF-R988 as an example, the nucleotide sequence encoding the heavy chain variable region of the scFv antibody of VEGF-R988 was PCR amplified and inserted into the Sca I+Kpn I (Fermentas) digested pSTEP2 vector harboring nucleotide sequences encoding the heavy chain signal peptide (SEQ ID NO: 45) (the amino acid sequence correlating thereto being SEQ ID NO: 37), including VEGF165-R988 heavy chain SEQ ID NO: 55 (part of VEGF165-R988 heavy chain SEQ ID NO: 57), and rabbit IgG1 constant region (SEQ ID NO: 9) by in-fusion method, thus the heavy chain (SEQ ID NO: 53) expression vector was obtained. The nucleotide sequence encoding the light chain variable region of the scFv antibody of VEGF-R988 was PCR amplified and inserted into the Sca I+BamH I (Fermentas) digested pSTEP2 vector harboring nucleotide sequences encoding the light chain signal peptide (SEQ ID NO: 46) (the amino acid sequence correlating thereto being SEQ ID NO: 38), including VEGF165-R988 light chain SEQ ID NO: 56 (part of VEGF165-R988 light chain SEQ ID NO: 58), and rabbit kappa constant region (SEQ ID NO: 10) by in-fusion method, thus the light chain (SEQ ID NO: 54) expression vector was obtained. The recombinant plasmids were extracted, and transfected into HEK-293 cells and cultured for expression for 7 days, and the culture supernatant was purified by a protein A purification column to obtain high-purity antibodies.

Primers for amplifying the heavy chain variable region:

| F1 | ACCAGGGTGCTGAGTCAGTCGGTGGAGGAGTCC |
| --- | --- |
| R1 | TGTGACCAGGGTACCTGGGCCCCA |

Primers for amplifying the light chain variable region:

| F2 | ACAGGAGTGCATAGTGAGCTCGATCTGACCCAGAC |
| --- | --- |
| R2 | GGTGCAACTGGATCCCCTTTGACGACCACCTCGGT |

1.4 Function Analysis of Rabbit Antibodies Targeting VEGF165

1.4.1 Rabbit Antibody Blocks VEGF165 from Binding to VEGFR2-his

VEGF165 protein (from SinoBiological, Inc.) at a concentration of 1 μg/mL was coated on a 96-well plate in 100 μL/well overnight at 4°C. The plate was washed the next day and blocked at room temperature for 1 h. 100 μL of 5 μg/mL VEGFR2-biotin protein (from SinoBiological, Inc.) and said rabbit antibodies targeting VEGF165 at different concentrations were added and co-incubated. The plate was washed to remove unbound antibodies, incubated with Streptavidin/HRP (from Beijing ZSGB-Bio Co., Ltd.) and then repeatedly washed, and the chromogenic substrate solution was added for color development. $OD_{450}$ was measured after the color development was ended. Taking the concentration of the rabbit antibody targeting VEGF165 as the horizontal coordinate and the inhibition rate PI % as the vertical coordinate, the GraphPad Prism 6.0 software was used for data analysis and generating a curve chart. Inhibition rate (%)=($OD_{blank}$−$OD_{sample}$)/$OD_{blank}$×100%, where $OD_{blank}$ indicates the OD value of the wells with only VEGFR2-biotin added but no rabbit antibody, and $OD_{sample}$ indicates the OD value of the wells with both VEGFR2-biotin and rabbit antibodies added.

As shown in FIG. 1, VEGFR2 protein can effectively bind to the coated VEGF165 protein, and the rabbit antibodies of VEGF-R859, VEGF-R988, VEGF-R613, VEGF-R812 can effectively inhibit the binding of VEGFR165 protein to VEGFR2 protein.

Antibody Inhibits the Proliferative Effect of VEGF 165 on Umbilical Vein Endothelial Cells 1.4.2 Rabbit Antibody Inhibits the Proliferation of HUVEC The effect of said rabbit antibodies neutralizing the VEGF 165-induced umbilical vein endothelial cells proliferation was detected by using the WST-8 method. Human umbilical vein endothelial cells HUVEC were inoculated into a 96-well plate at 4×10³ cells/well, cultured in M199 medium containing 10% FBS and 5% L-Gln for 4 h, and then different concentrations of rabbit antibodies were added in 50 μL/well, then VEGF-165 at a final concentration of 10 ng/mL was added in 10 μL/well, the 96-well plate was incubated in a 37° C., 5% $CO_2$ cell incubator for 3 days, and the blank well B (no cells), negative control M (cells inoculated, no antibody sample, VEGF-165 added) and M'(cells inoculated, no antibody sample and no VEGF-165) were used. After incubation, 10 μL/well of WST-8 chromogenic solution was added, and the 96-well plate was incubated in $CO_2$ incubator for color development, $OD_{450}$ and $OD_{630}$ were measured with a microplate reader after the color development was stabilized. For each well, the reading value was ($OD_{450}$-$OD_{630}$), and the neutralization rate of the antibody was calculated as the OD value for each group was defined as the reading value of the group minus the reading value of blank well B, the neutralization rate %=(OD value of negative control M−OD value of sample)/(OD value of negative control M−OD value of M')×100%. The standard curve was calculated using the automatic analysis function of the statistical software GraphPad Prism, taking the antibody sample concentration as the horizontal coordinate and the neutralization rate as the vertical coordinate, and the four-parameter logistic regression equation was used to fit the standard "S" curve to calculate the half-maximal effective concentration ($EC_{50}$) of the antibody sample.

Figure 2:
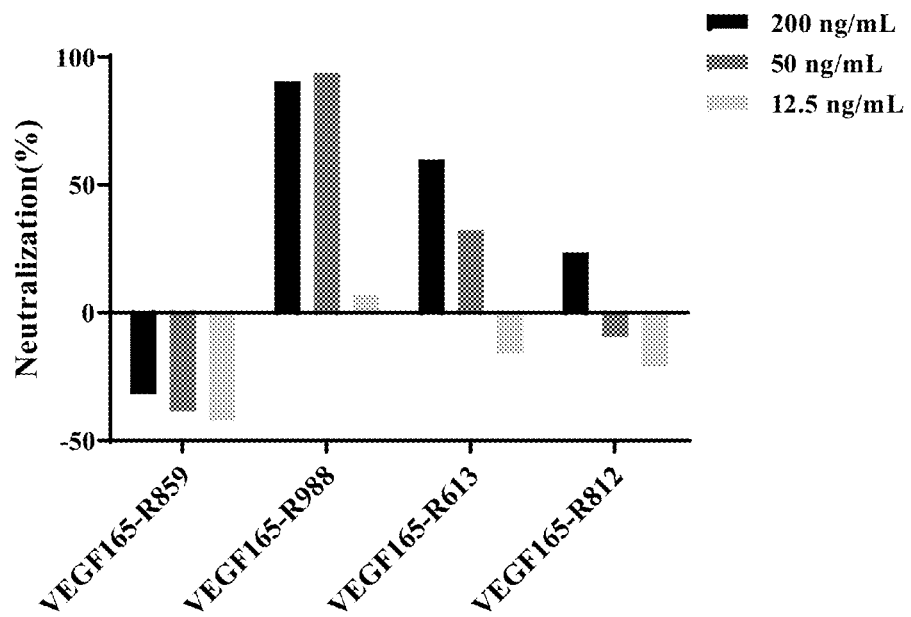
FIG. 2 shows that rabbit antibody VEGF165 neutralizes the VEGF165-induced the proliferation of HUVEC.

The results shown in FIG. 2 demonstrate that VEGF-R988 and VEGF-R613 effectively reduce the ability of VEGF165 to promoting HUVEC proliferation, and VEGF-R988 shows a higher maximum inhibition rate, VEGF-R812 has basically no inhibitory ability, while VEGF-R859 has no inhibitory ability at all.

Example 2: Humanization, Modification and Production of Rabbit Antibody VEGF-R988

On the ground of the results of the functional analysis of rabbit antibody in Example 1, VEGF-R988 was selected for humanization and production.

2.1 Determination of the CDRs of the Light and Heavy Chains of Rabbit Antibody VEGF-R988

Based on the nucleotide sequence of the VEGF-R988 scFv antibody determined in Example 1.2, the amino acid sequences of the heavy chain and light chain variable regions of the VEGF-R988 scFv were deduced, see SEQ ID NO: 11/12.

Refer to the Kabat index and IMGT numbering systems, the amino acid sequence of each of the three CDRs of the light and heavy chains of the rabbit antibody VEGF-R988-scFv were determined, see Table 1. The aforementioned respective three CDRs of the light chain and the heavy chain were transplanted into the humanized antibody VEGF-R988-scFv in the subsequent steps, see Example 2.2.

TABLE 1

CDR sequences of VEGF-R988 light chain and heavy chains

| Name | Sequences |
|---|---|
| LCDR1 | QSSQTIYANRRLA (SEQ ID NO: 13) |
| LCDR2 | GASTLAS (SEQ ID NO: 14) |
| LCDR3 | AGYKSYDGDDVG (SEQ ID NO: 15) |
| HCDR1 | GIDLSSYAISWV (SEQ ID NO: 16) |
| HCDR2 | YIWNAGNTYYASWAKG (SEQ ID NO: 17) |
| HCDR3 | ARGTLGDYNGMDP (SEQ ID NO: 18) |

2.2 CDR Transplantation of the Rabbit Antibody VEGF-R988

The humanization of the rabbit antibody was performed using the classic humanization method of CDR transplantation. The human antibody light or heavy chain variable region, whose sequence is closer to the sequence of rabbit light or heavy chain variable region, was elected as the template, and each of three CDRs (Table 1) from the rabbit light or heavy chain were inserted into the variable regions of the human antibody to obtain the humanized light chain variable region (VL) or heavy chain variable region (VH) sequences respectively. The human template for the light chain variable region of VEGF-R988 is IGKV1-27*01, which is 65.30% homologous to the light chain of VEGF-R988, and the human template for the heavy chain variable region is IGHV4-4*08, which is 53.20% homologous to the heavy chain of VEGF-R988.

2.3 Reverse-Mutations at the Framework Region of the Humanized Variable Region

As some key amino acids in the rabbit-derived framework region are essential to maintain the CDR activity, the key amino acids were reverse-mutated to the corresponding rabbit antibody amino acid sequences, the following sites were reversely mutated: in the light chain, Position 1 was reversely mutated to E, Position 2 was reversely mutated to L, Position 4 was reversely mutated to L, and Position 63 was reversely mutated to K; while in the heavy chain, Position 3 was reversely mutated to V, Position 37 was reversely mutated to V, Position 47 was reversely mutated to Y, Position 78 was reversely mutated to V, Position 79 was reversely mutated to D, and Position 91 was reversely mutated to F; all the above sites were numbered by reference to the Kabat numbering scheme. The humanized antibody VEGF-H988-10 was obtained by CDR humanized transplantation and framework region reverse-mutations.

2.4 Production of Humanized Monoclonal Antibody VEGF-H988-10 and CDR Affinity Modification VEGF-H988-10 heavy chain variable region (SEQ ID NO: 23) was obtained by the whole gene synthesis method, and then inserted, by in-fusion method, into Sca I+Nhe I (Fermentas) digested pSTEP2 vector harboring the nucleotide sequence encoding the heavy chain signal peptide (SEQ ID NO: 45) and the nucleotide sequence encoding the human IgG1 constant region (SEQ ID NO: 49), to obtain the VEGF-H988-10 heavy chain (SEQ ID NO: 19) (the corresponding amino acid sequence being SEQ ID NO: 21) expression vector. VEGF-H988-10 light chain variable region (SEQ ID NO: 24) was obtained by the whole gene synthesis method, and then inserted, by in-fusion method, into Sca I+BsiW I (Fermentas) digested pSTEP2 vector harboring the nucleotide sequence encoding the light chain signal peptide (SEQ ID NO: 46) and the nucleotide sequence encoding the human kappa constant region (SEQ ID NO: 50) to obtain the VEGF-H988-10 light chain (SEQ ID NO: 20) (the corresponding amino acid sequence being SEQ ID NO: 22) expression vector. Plasmids were extracted and co-transfected into HEK-293 cells, the cells were cultured for 7 days. The culture supernatant was purified with a protein A purification column to obtain high-purity antibodies.

Primers for whole gene synthesis of the heavy chain variable region

| F3 | CCACAGGAGTGCATAGTGAACTCCAACTTACCCAGAGCCCATCCTCCCTG |
| R3 | CCTGTCTCCCACAGAGGCAGACAGGGAGGATGG |
| F4 | TCTGTGGGAGACAGGGTGACCATCACTTGTCAG |
| R4 | GGCATAGATGGTCTGGCTGGACTGACAAGTGAT |
| F5 | CAGACCATCTATGCCAACAGGAGACTGG |
| R5 | TTCTGTTGATACCAAGCCAGTCTCCTGT |
| F6 | TTGGTATCAACAGAAGCCTGGCAAGGTG |
| R6 | AAATCAGCAGTTTTGGCACCTTGCCAGG |
| F7 | CAAAACTGCTGATTTATGGAGCCAGCAC |
| R7 | CACTCCAGATGCCAGGGTGCTGGCTCCA |
| F8 | CTGGCATCTGGAGTGCCAAGCAGGTTCAAGGGC |
| R8 | GAAGTCTGTGCCAGAGCCAGAGCCCTTGAACCT |
| F9 | TCTGGCACAGACTTCACCCTGACCATCTCCTCC |
| R9 | AGCCACATCCTCAGGTTGGAGGGAGGAGATGGT |
| F10 | CCTGAGGATGTGGCTACCTACTACTGTGCTGGC |
| R10 | ATCTCCATCATAGGACTTGTAGCCAGCACAGTA |
| F11 | TCCTATGATGGAGATGATGTGGGCTTTGGAGGA |
| R11 | GGTGCAGCCACCGTACGCTTAATCTCCACCTTGGTGCCTCCTCCAAAGCC |

Primers for whole gene synthesis of the light chain variable region

| F12 | GCTACCAGGGTGCTGAGTCAGTCTGTCCAGGAGTCTGGACCTGGACTGGTG |
| R12 | GGACAGGGTCTCAGATGGCTTCACCAGTCCAGG |
| F13 | TCTGAGACCCTGTCCCTGACTTGTACTGTGTCT |
| R13 | ATAGGAGGACAGGTCAATGCCAGACACAGTACA |

-continued

| | |
|---|---|
| F14 | GACCTGTCCTCCTATGCCATCTCCTGGGTGA |
| R14 | CCCTTGCCAGGAGGTTGTCTCACCCAGGAGA |
| F15 | ACCTCCTGGCAAGGGATTGGAATACATTGGC |
| R15 | TGCCAGCATTCCAGATGTAGCCAATGTATTC |
| F16 | TCTGGAATGCTGGCAACACCTACTATGCCTC |
| R16 | CACCCTGCCCTTAGCCCAGGAGGCATAGTAG |
| F17 | GCTAAGGGCAGGGTGACCATCTCTGTGGACACC |
| R17 | CAGGTCCACCTGGTTCTTGCTGGTGTCCACAGA |
| F18 | AACCAGGTGGACCTGAAACTGTCCTCTGTGACA |
| R18 | GTAGACTGCTGTGTCTGCTGCTGTCACAGAGGA |
| F19 | GACACAGCAGTCTACTTCTGTGCCAGGGGCACC |
| R19 | CATCCCATTGTAGTCTCCCAGGGTGCCCCTGGC |
| F20 | GACTACAATGGGATGGACCCATGGGGACCTGGC |
| R20 | GGGCCCTTGGTGCTAGCGCTGGACACTGTCACCAGGGTGCCAGGTCCCA |

To improve the affinity of VEGF-H988-10, SDM libraries of CDR regions of heavy and light chain variable regions (including three saturated mutation libraries of LCDR1, LCDR3, and HCDR2) were constructed; meanwhile, to improve the chemical stability of the antibody, the amino acid residues capable of undergoing deamidation or isomerization should be modified to another amino acid residue. The deamidation of asparagine can occur in, such as NG, NS, NA, NT, etc., leading to the generation of isoaspartic residues, which affects the stability or biological function of the antibody. The VEGF-H988 variable region HCDR3 has (a) deamidation-susceptible site(s), thus SDM libraries were constructed to improve the chemical stability and biological function of the antibody. The above four mutant libraries were constructed in scFv form and were cloned into phage vector as scFv-gIII fusion protein; for each CDR, the CDR clones having optimal binding ability to soluble antigen VEGF were screened, and finally the antibody VEGF-H988 having optimized CDR affinity and stability was obtained. The sequences of VEGF-H988 light and heavy chain CDRs are shown in Table 2.

TABLE 2

CDR sequences of VEGF-H988 light chain and heavy chains

| Name | Sequences |
|---|---|
| LCDR1 | QSSKFLWQGRRLA (SEQ ID NO: 27) |
| LCDR2 | GASTLAS (SEQ ID NO: 28) |
| LCDR3 | AGYKSYDGDVVG (SEQ ID NO: 29) |
| HCDR1 | GIDLSSYAIS (SEQ ID NO: 30) |
| HCDR2 | YIWNDLFTYYASWAKG (SEQ ID NO: 31) |
| HCDR3 | ARGTLGDYGGMDP (SEQ ID NO: 32) |

2.5 Production of Humanized Monoclonal Antibody VEGF-H988

The nucleotide sequence (SEQ ID NO: 44) encoding the aforementioned antibody VEGF-H988 light chain and the signal peptide (the corresponding amino acid sequence being SEQ ID NO: 36), which contains the following nucleotide sequences encoding light chain signal peptide (SEQ ID NO: 46), the humanized antibody light chain variable region (SEQ ID NO: 48) and the human antibody kappa light chain constant region (SEQ ID NO: 50) connected in order (the amino acid sequence of the light chain of humanized antibody VEGF-H988 was SEQ ID NO: 34), was PCR amplified and inserted into the self-developed pGS vector (Kpn I+Xba I) by in-fusion method, and the correct plasmids were verified by sequencing. The nucleotide sequence (SEQ ID NO: 43) encoding the aforementioned antibody VEGF-H988 heavy chain and the signal peptide (the corresponding amino acid sequence being SEQ ID NO: 35), which contains the following nucleotide sequences encoding heavy chain signal peptide (SEQ ID NO: 45), the humanized antibody heavy chain variable region (SEQ ID NO: 47) and the human antibody kappa heavy chain constant region (SEQ ID NO: 49) connected in order (the amino acid sequence of the heavy chain of humanized antibody VEGF-H988 was SEQ ID NO: 33), was PCR amplified and inserted into pGS vector (Nhe I+Not I) which had been verified to contain the light chain correctly by in-fusion method, and the correct vectors expressing both light and heavy chains of VEGF-R988 were verified by sequencing. These expression vectors are eukaryotic expression vectors containing the GS genes as the selection marker and the expression elements of the antibody light and heavy chains. These expression vectors were transfected into CHO-K1-GS-deficient cells and VEGF-H988 high expression cell lines were obtained by MSX screening. The clones with high antibody expression were selected by ELISA assay, and the high expression cell lines were selected by taking into account both the cell growth status and the key quality characteristics for antibody drugs. A serum-free suspension culture was used to culture the VEGF-H988 producing CHO cell line to obtain high purity and quality VEGF-H988 antibodies.

Example 3: Characteristic Analysis of Humanized Antibody VEGF-H988

3.1 Characteristic Analysis of Humanized Antibody VEGF-H988 Binding to VEGF165

3.1.1 Humanized Antibody VEGF-H988 Specifically Binds to VEGF165

Recombinant human VEGF165 protein (from SinoBiological, Inc.) in different concentrations (0.15 ng/ml, 0.46 ng/ml, 1.37 ng/ml, 4.12 ng/ml, 12.35 ng/ml, 37.04 ng/ml, 111.11 ng/mL, 333.33 ng/mL, 1000 ng/mL and 3000 ng/mL) was coated on a 96-well plate overnight at 4° C. in 100 µL/well. The plate was washed the next day and blocked at room temperature for 1 h. After incubation with 100 µL of 1 µg/mL of VEGF165-H988, Avastin (from Roche) or negative control antibody H7N9-R1 respectively, the plate was washed to remove unbound antibodies, then incubated with goat F(ab')2 anti-human IgG F(ab')2/HRP (from Jackson Immuno Research Laboratories, Inc.) and washed repeatedly, and the chromogenic substrate solution was added for color development. $OD_{450}$ was measured after the color development was ended. Taking the concentration of recombinant human VEGF165 protein as the horizontal coordinate and the $OD_{450}$ value as the vertical coordinate, the GraphPad Prism 6.0 software was used to fit an "S" curve chart and the binding of the antibody to recombinant human VEGF165 protein was analyzed.

Figure 3:
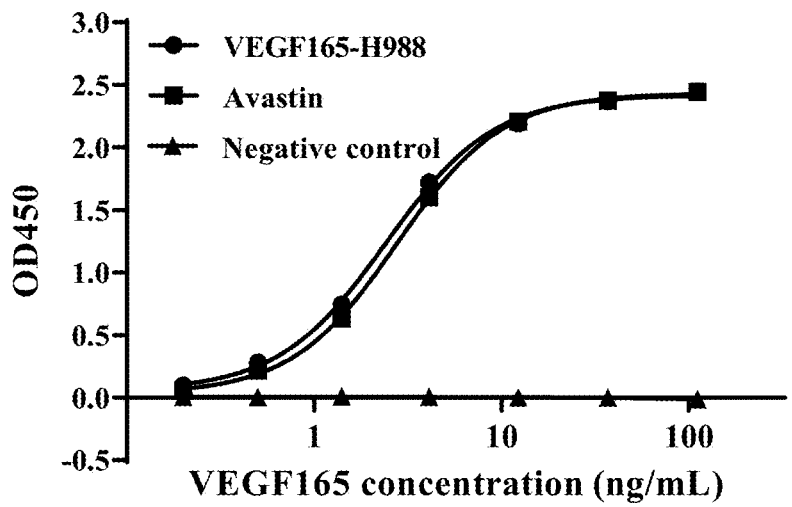
FIG. 3 shows the binding of humanized antibody VEGF165-H988 to VEGF165, detected by ELISA.

The results shown in FIG. 3 demonstrate that the $EC_{50}$ value of humanized molecule VEGF165-H988 specifically binding to recombinant human VEGF165 is 2.42 ng/mL, R2=0.999; the $EC_{50}$ value of Avastin binding to recombinant human VEGF165 is 2.77 ng/mL, R2=1.000. This indicates that the ability of VEGF165-H988 binding to recombinant human VEGF 165 protein is slightly better than that of Avastin. The negative control antibody H7N9-R1 has no binding ability to recombinant human VEGF165 protein.

3.1.2 Assay of the Binding Affinity of Humanized Antibody VEGF-H988 to Recombinant VEGF165 Protein The affinities of VEGF165-H988 and Avastin (from Roche) were measured at multiple concentrations using streptavidin-coated Sensor and immobilized biotin-labeled VEGF165 protein.

The recombinant human VEGF165 protein was first labeled with biotin in a molar ratio of 1:2 as the following process: the recombinant VEGF protein buffer (20 mM Tris, 150 mM NaCl, pH 8.0) was replaced with PBS through ultrafiltration in a 5000 MW ultrafiltration centrifugal tube, and 567.57 μg of protein was obtained as measured by UV quantification, and the resulting proteins were mixed with 20 mM biotin solution in a 1:2 molar ratio for incubation for 30 min at room temperature in the dark, then filtered again in a 5000 MW ultrafiltration centrifugal tube to remove the unlabeled biotin. After UV quantification, the biotin-labeled proteins were obtained by adding an equal volume of glycerol and a final concentration of 0.1% BSA. The concentration of the VEGF165 protein was 2.08 mg/mL, detected by UV.

Then the affinities of VEGF165-H988 and Avastin in different concentrations with biotinylated recombinant human VEGF proteins were measured, and the obtained KD values were the final affinities.

The results shown in Table 3 demonstrate that, the binding affinity KD value of VEGF165-H988 to recombinant human VEGF165 protein was 19.5 μM, the binding constant $k_{on}$ value was 3.44E±05 $M^{-1}s^{-1}$, and the dissociation constant $k_{dis}$ value was 6.70E-06 $s^{-1}$; the binding affinity KD value of Avastin to VEGF protein was 29.2E-11 pM, with a binding constant $k_{on}$ value of 1.87E±05 $M^{-1}s^{-1}$ and a dissociation constant $k_{dis}$ value of 5.46E-06 $s^{-1}$, as shown in Table 3. From the results, it can be concluded that the affinity of VEGF165-H988 is slightly higher than that of Avastin, i.e. about 1.5 times higher than the affinity of Avastin.

TABLE 3

The binding affinities of VEGF-H988 and Avastin with recombinant protein VEGF165

| Sample | KD(M) | $k_{on}(M^{-1}s^{-1})$ | $k_{dis}(s^{-1})$ |
|---|---|---|---|
| VEGF-H988 | 1.95E-11 | 3.44E+05 | 6.70E-06 |
| Avastin | 2.92E-11 | 1.87E+05 | 5.46E-06 |

3.1.3 Determination of Species Cross Reactivity of Humanized Antibody VEGF165-H988

Recombinant human VEGF165 proteins or recombinant mouse mVEGF164 proteins were diluted to 0.1 μg/mL, 1 μg/mL and 10 μg/mL, respectively, and coated on a 96-well plate overnight at 4° C. in 100 μL/well. The plate was washed the next day, blocked at room temperature for 1 h. 100 μL of VEGF165-H988, Avastin (from Roche) or negative control antibody H7N9-R1 was added respectively in a concentration of 1 μg/mL and incubated for 1 h. The plate was washed to remove unbound antibodies. The plate was incubated with goat F(ab')2 anti-human IgG F(ab')2/HRP (Jackson Immuno Research Laboratories, Inc.) and then repeatedly washed, and the chromogenic substrate solution was added for color development. $OD_{450}$ was measured after the color development was ended. Taking the protein concentration as the horizontal coordinate and the $OD_{450}$ value as the vertical coordinate, the GraphPad Prism 6.0 software was used for generating a bar chart.

Figure 4:
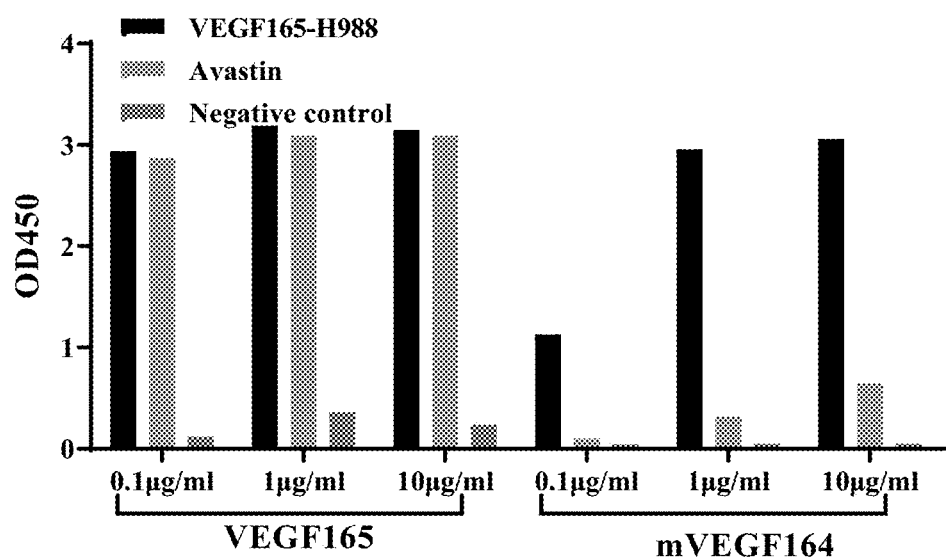
FIG. 4 shows the binding of humanized antibody VEGF165-H988 to VEGF165, detected by ELISA.

The results shown in FIG. 4 demonstrate that VEGF165-H988 binds to recombinant human VEGF165 protein specifically and show cross-binding with recombinant mouse mVEGF164 protein.

3.2 Receptor Blocking Properties of Humanized Antibody VEGF-H988

VEGF165 protein (from SinoBiological, Inc.) at a concentration of 1 μg/mL was coated on a 96-well plate in 100 μL/well overnight at 4° C. The plate was washed the next day and blocked at room temperature for 1 h. 100 μL of 2 μg/mL VEGFR2-his protein (from SinoBiological, Inc.) was added in each well and different concentrations of antibody VEGF-H988, EYLEA, Avastin (from Roche) or negative control antibody H7N9-R1 was added respectively and co-incubated. The plate was washed to remove unbound antibodies. The plate was incubated with C-his-R023/HRP and then repeatedly washed, and the chromogenic substrate solution was added for color development. $OD_{450}$ was measured after the color development was stabilized, with each group tested in duplicate. Taking the concentration of the antibody as the horizontal coordinate and the inhibition rate PI % as the vertical coordinate, the GraphPad Prism 6.0 software was used for data analysis and generating a curve chart to calculate the IC50 value. Inhibition rate (%)= $(OD_{blank}-OD_{sample})/OD_{blank} \times 100\%$, where $OD_{blank}$ indicates the OD value of the wells with only VEGFR2-his added but no humanized antibody added, and OD sample indicates the OD value of the wells with both VEGFR2-his and the humanized antibodies added.

Figure 5:
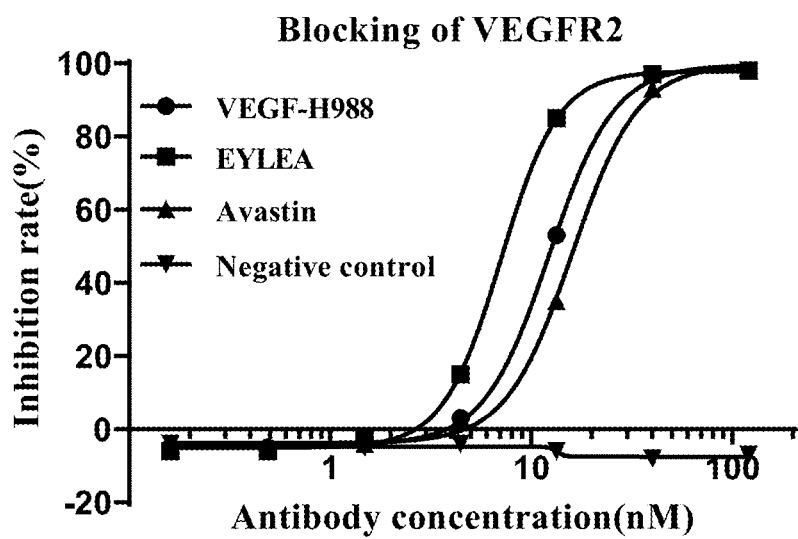
FIG. 5 shows that the antibody VEGF-H988 blocks the binding of VEGF165 to VEGFR2 protein, detected by ELISA.
Figure 6A:
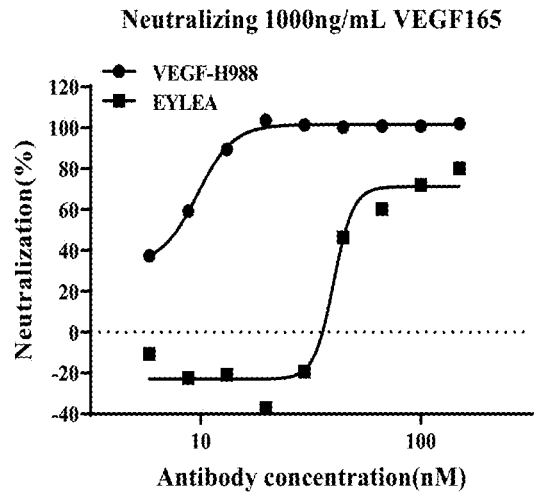
FIG. 6A shows the effect of antibody VEGF-H988 and EYLEA in neutralizing VEGF165 at a concentration of 1,000 ng/mL.
Figure 6B:
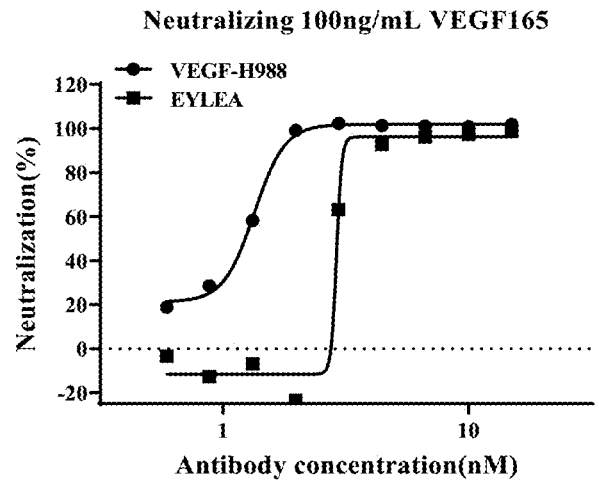
FIG. 6B shows the effect of antibody VEGF-H988 and EYLEA in neutralizing VEGF165 at a concentration of 100 ng/mL.
Figure 6C:
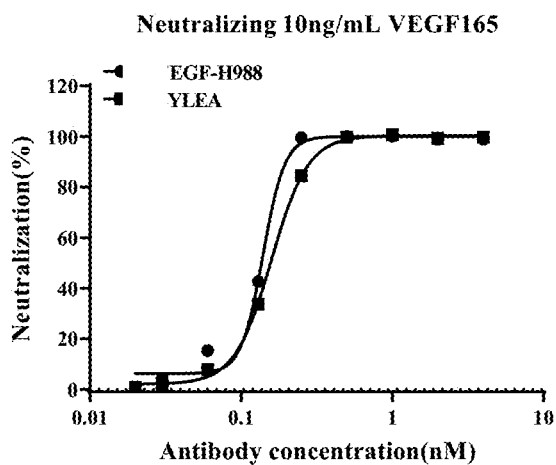
FIG. 6C shows the effect of antibody VEGF-H988 and EYLEA in neutralizing VEGF165 at a concentration of 10 ng/mL.
Figure 6D:
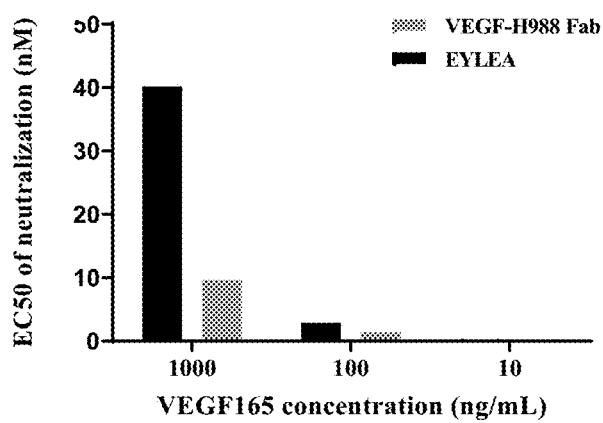
FIG. 6D shows EC50 values of neutralization calculated from the experiments from FIGS. 6A-6C.
Figure 6E:
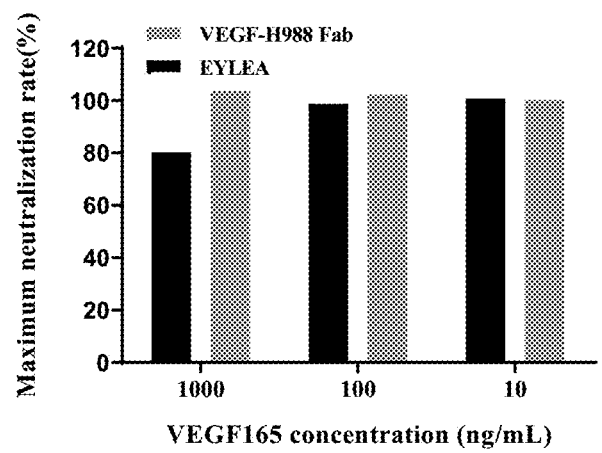
FIG. 6E shows the maximum neutralization rates from the experiments from FIGS. 6A-6C.
Figure 7A:
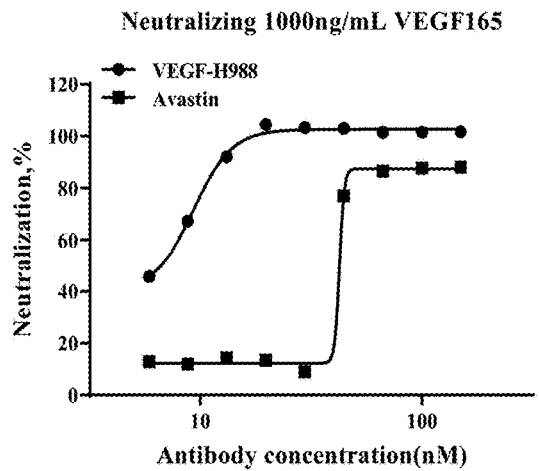
FIG. 7A shows the effect of antibody VEGF-H988 and Avastatin in neutralizing VEGF165 at a concentration of 1,000 ng/mL.
Figure 7B:
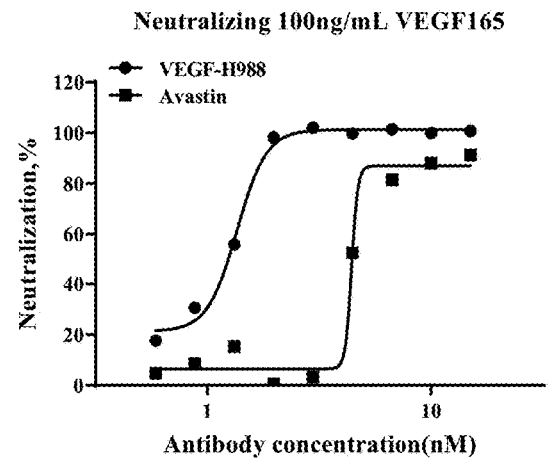
FIG. 7B shows the effect of antibody VEGF-H988 and Avastatin in neutralizing VEGF165 at a concentration of 100 ng/mL.
Figure 7C:
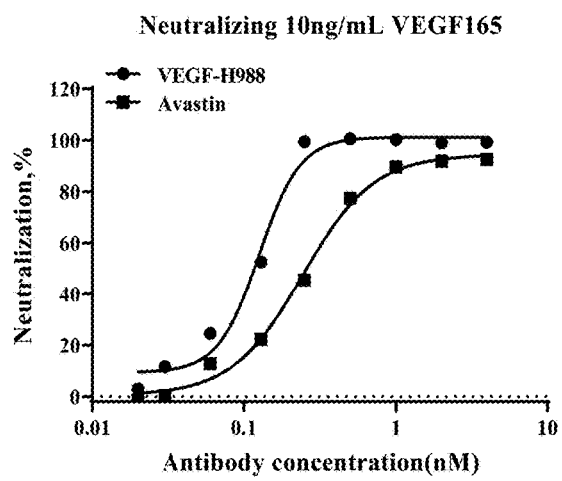
FIG. 7C shows the effect of antibody VEGF-H988 and Avastatin in neutralizing VEGF165 at a concentration of 10 ng/mL.
Figure 7D:
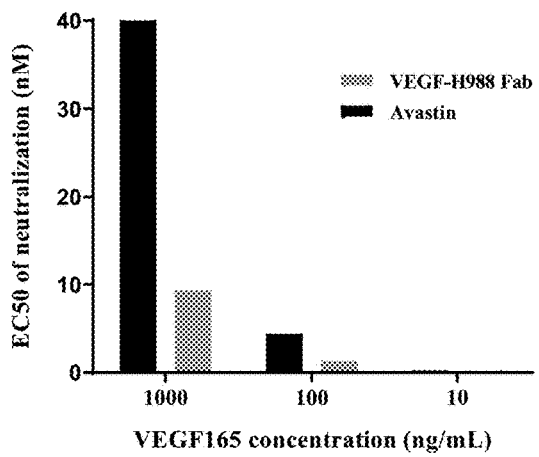
FIG. 7D shows EC50 values of neutralization calculated from the experiments from FIGS. 7A-7C.
Figure 7E:
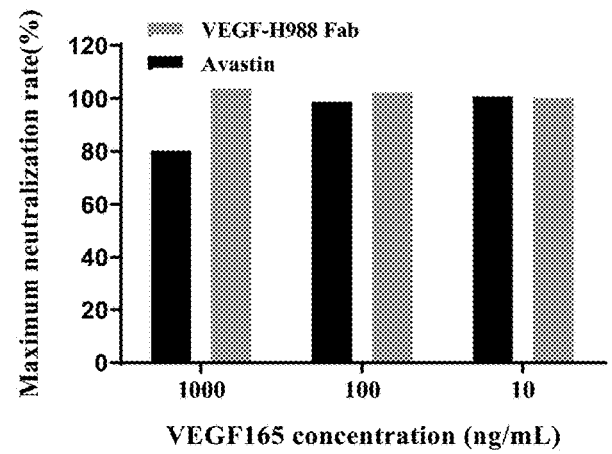
FIG. 7E shows the maximum neutralization rates from the experiments from FIGS. 7A-7C.

As shown in FIG. 5, VEGFR2 protein could effectively bind to the coated VEGF165 protein, and the antibodies VEGF-H988 could effectively inhibit the binding of VEGFR2 protein to VEGFR165 protein, with a relatively weaker inhibitory ability than EYLEA but greater than Avastin, and the negative control antibody has no inhibitory effect.

3.3 Inhibition of the Proliferation of HUVEC Cells by Humanized Antibody 3.3.1 Neutralization Effect of VEGF165 in Different Concentrations by Humanized Antibody VEGF-H988

The effect of VEGF-H988 neutralizing the VEGF 165-induced HUVEC cells proliferation was detected by using the WST-8 method. HUVEC cells were inoculated into a 96-well plate at 4×103 cells/well, cultured in M199 medium containing 10% FBS and 5% L-Gln for 4 h, and then VEGF-H988, EYLEA or Avastin (from Roche) in different concentrations were added in 50 μL/well, then VEGF-165 at the final concentrations of 1000 ng/ml, 100 ng/mL or 10 ng/ml were added in 10 μL/well, the 96-well plate was incubated in a 37° C., 5% CO2 cell incubator for 3 days, and the blank well B (no cells), negative control M (cells inoculated, no antibody sample added, VEGF-165 added) and M'(cells inoculated, no antibody sample added and no VEGF-165 added) were used. After incubation, 10 μL/well of WST-8 chromogenic solution was added, and the 96-well plate was incubated in $CO_2$ incubator for color development, $OD_{450}$ and $OD_{630}$ were measured with a microplate reader after the color development was stabilized. For each well, the reading value was ($OD_{450}$-$OD_{630}$), and the neutralization rate of the antibody was calculated as the OD value for each group was defined as the reading value of the group minus the reading value of blank well B, the neutralization rate %=(OD value of negative control M−OD value of sample)/(OD value of negative control M−OD value of M')×100%. The standard curve was calculated using the automatic analysis function of the statistical software GraphPad Prism, taking the antibody sample concentration as the horizontal coordinate and the neutralization rate as the vertical coordinate, and the 4-parameter logistic regression equation was used to fit the standard "S" curve to calculate the half-maximal effective concentration ($EC_{50}$) of the antibody sample.

As shown in FIGS. 6 and 7, antibody VEGF-H988 can effectively reduce the ability of VEGF165 to promoting HUVEC proliferation. The neutralizing ability of VEGF-H988 was stronger than that of EYLEA and Avastin at different concentrations of recombinant human VEGF165; and the difference of the neutralizing ability was stronger as the concentrations of VEGF165 is higher. Under the condition of high concentrations of VEGF165, VEGF-H988 still has a low neutralizing $EC_{50}$ and could still maintain the maximum neutralization rate, while the neutralizing $EC_{50}$ of EYLEA and Avastin gradually increased and was accompanied by a decrease of the maximum neutralization rate. The half-maximal effective concentrations ($EC_{50}$) and maximum neutralization rates of each antibody neutralizing VEGF165 in different concentrations are summarized in Table 4.

TABLE 4

$EC_{50}$ and maximum neutralization rate of VEGF-H988 neutralizing VEGF-165 of different concentrations

| VEGF165 concentration | Sample | $EC_{50}$(nM) | maximum neutralization rate (%) |
|---|---|---|---|
| 1000 ng/mL | VEGF-H988 | 9.67 | 103.7 |
| | EYLEA | 40.18 | 80.2 |
| 100 ng/mL | VEGF-H988 | 1.34 | 102.3 |
| | EYLEA | 2.90 | 98.7 |
| 10 ng/mL | VEGF-H988 | 0.14 | 100.2 |
| | EYLEA | 0.16 | 100.7 |
| 1000 ng/mL | VEGF-H988 | 9.33 | 104.5 |
| | Avastin | 42.49 | 88.1 |
| 100 ng/mL | VEGF-H988 | 1.36 | 102.1 |
| | Avastin | 4.40 | 91.3 |
| 10 ng/mL | VEGF-H988 | 0.13 | 100.5 |
| | Avastin | 0.24 | 92.5 |

3.3.2 Neutralization Effect of Different Subtypes of VEGFs by Humanized Antibody VEGF-H988

The WST-8 method was used to detect the effect of VEGF-H988 neutralizing different subtypes of VEGF (VEGF165, VEGFC and VEGFD)-induced HUVEC cells proliferation. HUVEC cells were inoculated into a 96-well plate at $4 \times 10^3$ cells/well, cultured in M199 medium containing 10% FBS and 5% L-Gln for 4 h, and then different concentrations of VEGF-H988 or Avastin (from Roche) were added in 50 μL/well, then VEGF-165, VEGFC and VEGFD mixture (the final concentrations were 25 ng/ml. 1000 ng/mL. 6000 ng/ml respectively) was added in 10 μL/well, the 96-well plate was incubated in a 37° C., 5% $CO_2$ cell incubator for 3 days, and the blank well B (no cells), negative control M (cells inoculated, no antibody sample added, VEGFs added) and M'(cells inoculated, no antibody sample and no VEGFs) were used. After incubation, 10 μL/well of WST-8 chromogenic solution was added, and the 96-well plate was incubated in $CO_2$ incubator for color development, $OD_{450}$ and $OD_{630}$ were measured with a microplate reader after the color development was stabilized. For each well, the reading value was ($OD_{450}$-$OD_{630}$), and the neutralization rate of the antibody was calculated as the OD value for each group was defined as the reading value of the group minus the reading value of blank well B, the neutralization rate %=(OD value of negative control M−OD value of sample)/(OD value of negative control M−OD value of M')×100%. The standard curve was calculated using the automatic analysis function of the statistical software GraphPad Prism, taking the antibody sample concentration as the horizontal coordinate and the neutralization rate as the vertical coordinate, and the 4-parameter logistic regression equation was used to fit the standard "S" curve to calculate the half-maximal effective concentration ($EC_{50}$) of the antibody sample.

Figure 8:
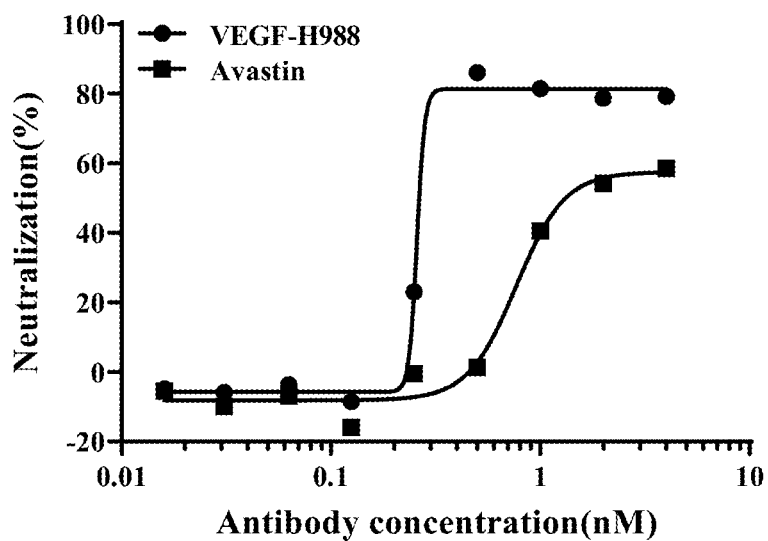
FIG. 8 shows the effect of VEGF-H988 on the neutralization of VEGF165, VEGFC and VEGFD-induced the proliferation of HUVEC cells.

As shown in FIG. 8, in the case of different subtypes of VEGF (VEGF165, VEGFC, VEGFD) acting simultaneously on HUVEC cells, antibody VEGF-H988 has a stronger neutralizing effect than Avastin. In the concentration range of 0.016-4.000 nM, VEGF-H988 has a smaller $EC_{50}$ than Avastin, being 0.26 nM and 0.77 nM, respectively; and VEGF-H988 has a higher neutralization rate than Avastin, being 86.1% and 58.5% respectively. The half-maximal effective concentrations ($EC_{50}$) and the maximum neutralization rates of VEGF and Avastin to neutralize different subtypes of VEGF are summarized in Table 5.

TABLE 5

EC50 and maximum neutralization rate of VEGF-H988 neutralizing different subtypes of VEGF

| Antibody | $EC_{50}$(nM) | Maximum neutralization rate Emax (%) |
|---|---|---|
| VEGF-H988 | 0.26 | 86.1 |
| Avastin | 0.77 | 58.5 |

Example 4: Repeated Administration Toxicity Study of Antibody VEGF-H988 in Mice

CD-1 mice, 8 each in the aged group (35 weeks of age) and normal group (9 weeks of age), half male and half female, were used. The mice were divided into four groups (G1-G4) according to the complete randomization method, with four mice in each group and half of the males and half of the females. The specific grouping was as follows: G1: old mice solvent control group; G2: old mice study group; G3: normal mice solvent control group; G4: normal mice study group. The VEGF-H988 antibodies were repeatedly administered to the study groups, and the control groups were given an equal volume of solvent. The dose was 50 mg/kg, the volume of each administration was 5 mL/kg (1st to 8th dose) and 10 mL/kg (9th to 16th dose), respectively; the mode of administration was intraperitoneal injection, with a frequency of twice weekly. All mice were subjected to orbital blood sampling before and 0.5 h, 2 h, 4 h, 6 h, 24 h, 48 h, 72 h after the first dosing as well as before and 1 h after every other dosing, for pharmacokinetic and immunogenicity assays. The body weights of mice were measured and recorded before each dosing. The detailed dosing regimen is shown in Table 6.

TABLE 6

Dosing regimen of antibody VEGF-H988

| Group | Antibody | Dose | Mode of administration | Frequency of administration | Mice status |
|---|---|---|---|---|---|
| G1 | None (solvent control group) | 0 mg/kg | i.p. | Twice weekly | 2 ♀ & 2 ♂ (aged) |
| G2 | VEGF-H988 | 50 mg/kg | i.p. | Twice weekly | 2 ♀ & 2 ♂ (aged) |
| G3 | None (solvent control group) | 0 mg/kg | i.p. | Twice weekly | 2 ♀ & 2 ♂ (normal age) |
| G4 | VEGF-H988 | 50 mg/kg | i.p. | Twice weekly | 2 ♀ & 2 ♂ (normal age) |

The body weights of the mice in the antibody VEGF-H988 groups were similar to those of the corresponding solvent control groups, indicating that the antibody VEGF-H988 had no effect on the body weight of the mice. During the study, the clinical abnormalities were observed in the antibody VEGF-H988 groups. All mice were subjected to gross autopsy, and there were no visible abnormalities in the tissues and organs. Histopathological examination showed that all mice had venous congestion in the liver, lungs, and kidneys, but there was no significant difference between the control groups and the study groups. Sparse individual mice showed pink serous or erythrocyte stasis in the spleen and the inflammatory cell infiltration in the kidneys, which were considered to be individual difference and not related to drug administration. The toxicokinetic parameters of mice after the first dose are summarized in Table 7.

In addition, the abnormal blood drug concentration at 1 h after administration may also be related to the drug distribution speed in vivo and individual differences.

Although the immunogenicity test results showed positives in part of subjects, the difference between the SNR and the threshold SCP was small, actually, they are very closely, thus a strong positive is not shown, and it is considered that the aforesaid positive results were probably false positives. Table 8 summarizes the immunogenicity results of the repeated dosing toxicity study of the antibody VEGF-H988 in mice.

TABLE 7

Toxicokinetic parameters of toxicity study of repeated administration in mice

| Group | Gender | / | t1/2 (h) | Tmax (h) | Cmax (μg/mL) | AUClast (h × μg/mL) | AUC0-∞ (h × μg/mL) | Vz_F (mL/kg) | Cl_F (mL/h/kg) | MRTlast (h) |
|---|---|---|---|---|---|---|---|---|---|---|
| G2 (Aged) | ♂ | Mean | 53.246 | 4.000 | 408.899 | 11735.125 | 14696.594 | 263.934 | 3.469 | 26.128 |
| | | SD | 5.161 | 0.000 | 63.837 | 1381.429 | 2880.380 | 26.398 | 0.680 | 4.929 |
| | ♀ | Mean | 55.751 | 2.000 | 435.691 | 12033.935 | 15499.970 | 254.922 | 3.276 | 26.934 |
| | | SD | 20.717 | 0.000 | 25.122 | 975.896 | 2717.582 | 51.721 | 0.574 | 0.748 |
| | ♀&♂ | Mean | 54.499 | 3.000 | 422.295 | 11884.530 | 15098.282 | 259.428 | 3.372 | 26.531 |
| | | SD | 12.411 | 1.155 | 42.521 | 991.632 | 2332.899 | 33.927 | 0.526 | 2.916 |
| G4 (Normal age) | ♂ | Mean | 50.699 | 4.000 | 299.521 | 11327.725 | 14664.044 | 254.388 | 3.475 | 31.698 |
| | | SD | 0.516 | 0.000 | 47.342 | 2175.405 | 2832.204 | 51.669 | 0.671 | 0.440 |
| | ♀ | Mean | 80.867 | 4.000 | 202.054 | 9150.110 | 15211.402 | 469.071 | 3.873 | 37.243 |
| | | SD | 11.207 | 0.000 | 143.203 | 5988.595 | 8367.579 | 311.174 | 2.130 | 1.557 |
| | ♀&♂ | Mean | 65.783 | 4.000 | 250.788 | 10238.918 | 14937.723 | 361.730 | 3.674 | 34.471 |
| | | SD | 18.583 | 0.000 | 103.679 | 3887.487 | 5110.035 | 220.294 | 1.310 | 3.335 |

Figure 9:
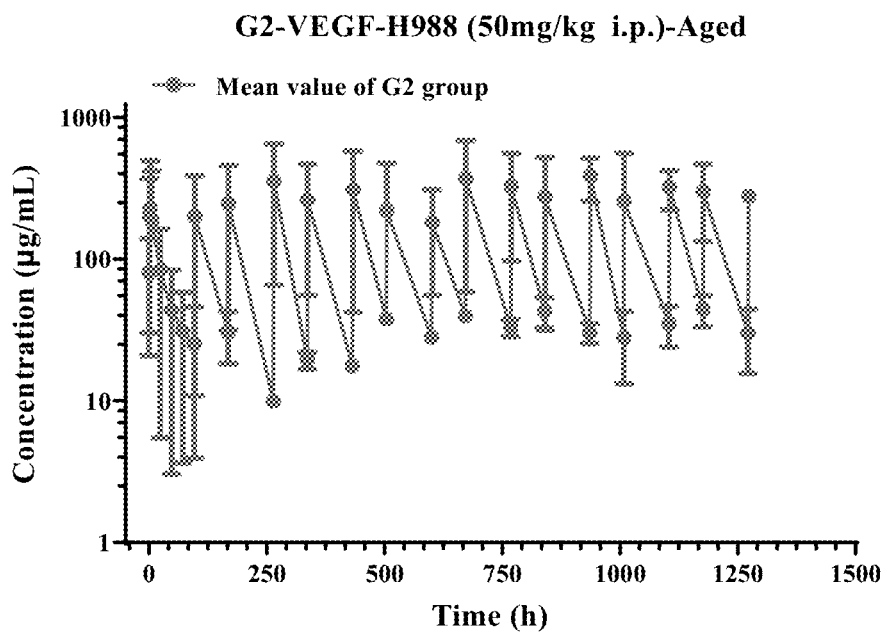
FIG. 9 shows the mean blood concentration-time curve of G2 group mice injected with VEGF-H988 (50 mg/kg) intraperitoneally.
Figure 10:
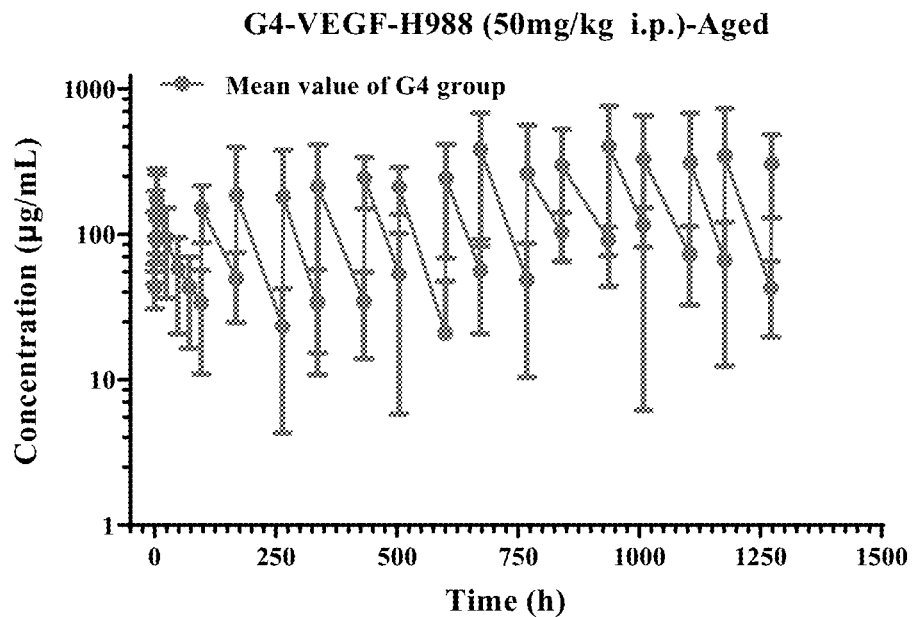
FIG. 10 shows the mean blood concentration-time curve of G4 group mice injected with VEGF-H988 (50 mg/kg) intraperitoneally.
Figure 11:
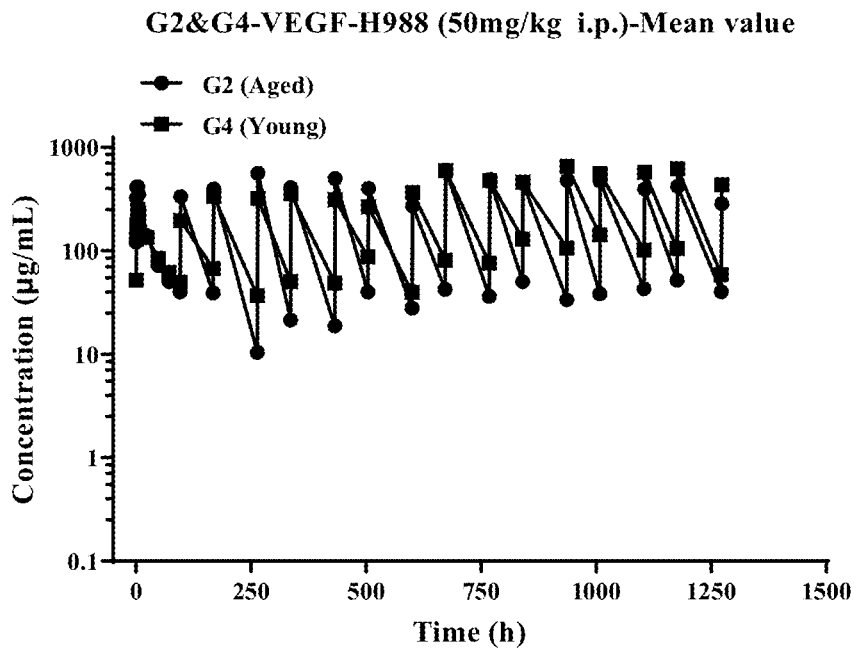
FIG. 11 shows the mean blood concentration-time curve of G2&G4 groups mice injected with VEGF-H988 (50 mg/kg) intraperitoneally.

As shown in the blood drug concentration-time curve in FIGS. 9-11, there was no significant difference in the trend of blood concentration changes between male and female animals in each group. There was no significant accumulation after multiple dosing in both groups, which may be related to the higher dose administered groups having reached saturation levels. The peak blood concentrations in the G2 group (aged) and the G4 group (normal) were basically the same, and the trough concentrations in the aged group were slightly lower, which may be related to the large individual differences within the group.

Mice in each group showed no significant increase or even some decrease in the blood drug concentration at 1 h after administration, which did not correlate well with immunogenicity (see Table 8 for immunogenicity test data).

TABLE 8

Immunogenicity test results of toxicity study of repeated administration of VEGF-H988 in mice

| Time point | | 0 h | | 432 h | |
|---|---|---|---|---|---|
| Group | Mouse No. | SNR | Conclusion | SNR | Conclusion |
| G2 (Aged) | 69 | 0.791 | − | 0.814 | − |
| | 78 | 1.140 | + | 0.919 | − |
| | 64 | 0.791 | − | 0.791 | − |
| | 63 | 1.058 | + | 0.977 | − |
| G4 (Normal) | 88 | 0.814 | − | 0.860 | − |
| | 87 | 0.767 | − | 0.895 | − |
| | 89 | 0.884 | − | 1.070 | + |
| | 84 | 0.791 | − | 0.907 | − |

Repeated administration toxicity tests in mice showed that no significant drug-related toxic effects were observed when the antibody VEGF-H988 was repeatedly administered at a dose of 50 mg/kg twice weekly via intraperitoneal injection to aged CD-1 mice and normal CD-1 mice for 16 doses.

Example 5: Efficacy Study in Human Colorectal Cancer Cell Line HCT-116 Xenograft Tumor Model Female Balb/c-nu nude mice were from Beijing Vital River Laboratory Animal Technology Co., Ltd. (Animal production license No. SCXK (Beijing) 2016-0006, Quality certificate No. 11400700373019). HCT116 tumor blocks were obtained from mice inoculated with self-developed HCT116 cell line. Balb/c-nu 6-week-old female mice were inoculated subcutaneously with HCT116 tumor blocks of approximately 2×2×2 (mm3) in size, and when the tumor volume reached approximately 300 mm3, the mice were administered in groups with intraperitoneal injection of 1 mg/kg of VEGF-H988 or Avastin (from SinoCelltech Co., Ltd.) or the corresponding solvent, respectively twice weekly. Tumor volumes were measured twice weekly to assess the antitumor efficacy of VEGF-H988 versus Avastin.

Figure 12:
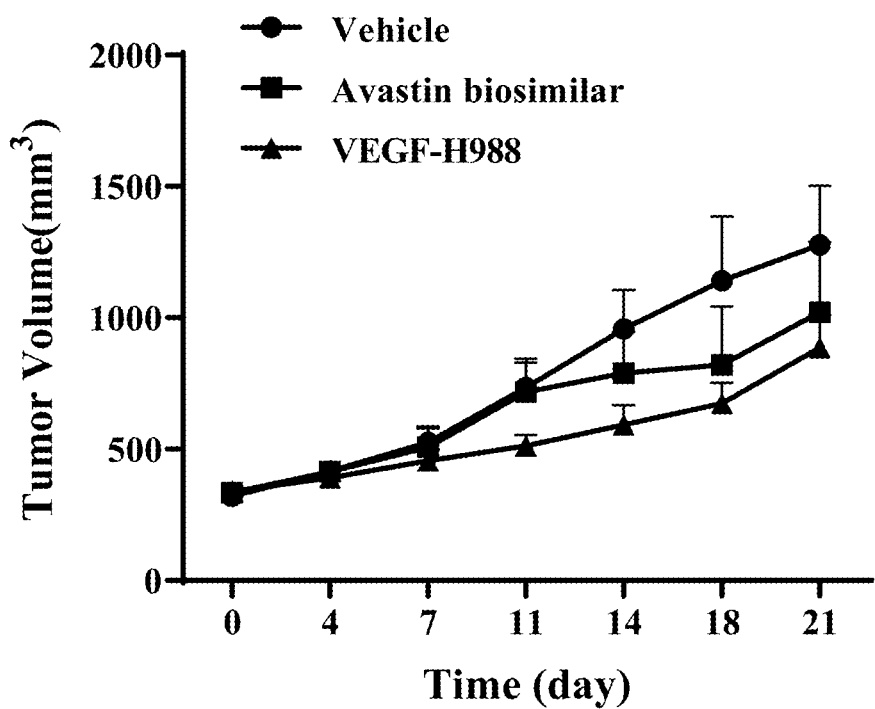
FIG. 12 shows the comparison of the efficacies of VEGF-H988 and the control drugs in the human colorectal cancer cell line HCT-116 xenograft tumor model.

As shown in FIG. 12, in the case of a larger initial tumor volume of about 300 mm3 and a lower dose (1 mg/kg), the tumor growth rate was progressively reduced in the VEGF-H988-treated group compared to the non-dosed control group since Day 7 after administration. The inhibitory effect of Avastin on tumor growth began on the 11th day after administration, later than that in the equivalent dose of VEGF-H988 treated group. Tumor inhibition assays in the HCT-116 xenograft tumor model showed that the inhibitory effect of VEGF-H988 on tumor growth is better than that of Avastin.

SEQUENCE LISTING

```
<160> NUMBER OF SEQ ID NOS: 98

<210> SEQ ID NO 1
<211> LENGTH: 191
<212> TYPE: PRT
<213> ORGANISM: Homo sapiens

<400> SEQUENCE: 1

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg
            180                 185                 190

<210> SEQ ID NO 2
<211> LENGTH: 54
<212> TYPE: DNA
<213> ORGANISM: Artificial Sequence
<220> FEATURE:
<223> OTHER INFORMATION: Nucleotide sequence of the linker used in the
      construction of the phage antibody library for the linkage of the
      rabbit antibody scFv
```

<400> SEQUENCE: 2

```
tctagtggtg gcggtggttc gggcggtggt ggaggtggta gttctagatc ttcc        54
```

<210> SEQ ID NO 3
<211> LENGTH: 732
<212> TYPE: DNA
<213> ORGANISM: Artificial Sequence
<220> FEATURE:
<223> OTHER INFORMATION: Nucleotide sequence of rabbit antibody scFv
      used in the construction of antibody VEGF165-R859

<400> SEQUENCE: 3

```
gatgtcgtga tgacccagac tgcagcctcc gtgtctgaac ctgtgggagg cacagtcacc    60
atcaagtgcc aggccagtca gagcattagg agttggttat cctggtatca gcagaaacca   120
gggcagcctc ccaagctcct gatctatcag gcatccaaat ggcatctggg gtcccatcg    180
cggttcaaag gcagtggata tgggacagag ttcactctca ccatcagcga cctggagtgt   240
gccgatgctg ccacttacta ctgtcaaaac aattattctt ttagtaaaga tggtggtgct   300
ttcggcggag ggaccgaggt ggtcgtcaaa tctagtggtg gcggtggttc gggcggtggt   360
ggaggtggta gttctagatc ttcccagtcg gtggaggagt ccgggggtcg cctggtcacg   420
cctgggacac ccctgacact cacctgccaa gtctctggat tctccctcaa catctacgac   480
atgacctggg tccgccaggc tccagggaag gggctggaat ggatcggaat cattgcgcct   540
gatgatagcg catactacgc gaactgggcg aaaggccgat tcaccatctc caaaacctcg   600
accacggtgg atctgaaaat gaccagtccg acaaccgagg cacggccac ctatttctgt    660
gccagaaatg cctatagtag tggctggggt ggggacttgt ggggcccagg caccctggtc   720
actgtctctt ca                                                        732
```

<210> SEQ ID NO 4
<211> LENGTH: 738
<212> TYPE: DNA
<213> ORGANISM: Artificial Sequence
<220> FEATURE:
<223> OTHER INFORMATION: Nucleotide sequence of the rabbit antibody scFv
      used in the construction of antibody VEGF165-R988

<400> SEQUENCE: 4

```
gagctcgatc tgacccagac tccatccccc gtgtctgcgg ctgttggagg cacagtcacc    60
atcaattgcc agtccagtca gactatttat gctaacaggc gcttagcctg gtatcaacag   120
aaaccagggc agcctcccaa gctcctgatc tatggtgcat ccactctggc atctggggtc   180
ccatcgcggt tcaaaggcag tggatctggg acacagttca ctctcaccat cagcggcgtg   240
cagtgtgacg atgctgccac ttactactgt gcaggctata aaagttatga tggtgatgat   300
gttggtttcg gcggagggac cgaggtggtc gtcaaatcta gtggtggcgg tggttcgggc   360
ggtggtggag gtggtagttc tagatcttcc cagtcggtgg aggagtccgg gggtcgcctg   420
gtaacgcctg gacacccct gacactcacc tgcacagtct ctggaatcga cctcagtagc   480
tatgcaataa gctgggtccg ccaggctcca gggaaggggc tggaatacat cggatacatt   540
tggaatgctg gtaacaccta ctacgcgagc tgggcaaaag ccgattcac catctccaaa    600
acctcgacca cggtggatct gaaaatcacc agtccgacaa ccgaggacac ggccacctat   660
ttctgtgcca gaggaacatt agggactac aatggcatgg accctgggg cccagggacc     720
ctcgtcaccg tctcttca                                                  738
```

<210> SEQ ID NO 5
<211> LENGTH: 738
<212> TYPE: DNA
<213> ORGANISM: Artificial Sequence
<220> FEATURE:
<223> OTHER INFORMATION: Nucleotide sequence of the rabbit antibody scFv used in the construction of antibody VEGF165-R613

<400> SEQUENCE: 5

```
gagctcgtga tgacccagac tccatccccc gtgtctgcgg ctgttggagg cacagtcacc     60
atcaattgcc agtccagtca gagtgtttat agtaacaacc ggttagcctg gtatcagcag    120
aaaccagggc agcctcccaa gctcctgatc tatggtgcat ccactctggc atctggggtc    180
ccatcgcggt tcaaaggcag tggatctggg acacagttca ctctcaccat cagcgacgtg    240
cagtgtgacg atgctgccac ttactactgt gcaggctata aaagttatga tggtgatgat    300 gttggttttcg gcggagggac cgaggtggtg gtcaaatcta gtggtggcgg tggttcgggc    360
ggtggtggag gtggtagttc tagatcttcc cagtcggtgg aggagtccgg gggtcgcctg    420
gtcacgcctg gacacccct gacactcacc tgcacagtct ctggaatcga cctcagtagc    480
tatgcaataa gctgggtccg ccaggctcca gggaaggggc tggaatacat cggatacatt    540
tggagtactg ataacaccta ctatgcgagc tgggcaaaag ccgattcac catctccgag    600 gcctcgacca cggtggatct gaaaatcacc agcccgacaa ccgaggacac ggccacctat    660
ttctgtgcca aggaacgtt aggggactac aatggcatgg accctgggg cccagggacc    720 ctcgtcaccg tctcttca                                                 738
```

<210> SEQ ID NO 6
<211> LENGTH: 738
<212> TYPE: DNA
<213> ORGANISM: Artificial Sequence
<220> FEATURE:
<223> OTHER INFORMATION: Nucleotide sequence of the rabbit antibody scFv used in the construction of antibody VEGF165-R812

<400> SEQUENCE: 6

```
gagctcgtgc tgacccagac tccagcctcc gtggaggcag ctgtgggagg cacagtcacc     60
atcaagtgcc aggccagtca gagcattaat agttggttat cctggtatca gcagaaacca    120
gggcagcgtc ccaagctcct gatctaccag gcatccaaac tggcatctgg ggtcccatcg    180
cggttcaaag gcagtggatc tgggacagag tacactctca ccatcagcga cctggagtgt    240
gccgatgctg ccacttatta ctgccagaac aatcttggtg gtggtgatgg tagttatggt    300
cttcctttcg gcggagggac cgaggtggtg gtcaaatcta gtggtggcgg tggttcgggc    360
ggtggtggag gtggtagttc tagatcttcc cagtcgttgg aggagtccgg gggtcgcctg    420
gtaacgcctg gaggctccct gacactcacc tgcacagcct ctggattcga cctcggtatc    480
tatgaaataa cctgggtccg ccaggctcca gggaaggggc tggaatggat cggagtcatt    540
tatggtgatg gtgacacagt ctacgcgaac tgggcgaaag ccgattcac catctccaaa    600 acctcgacca cggtggatct gaaaatctcc agtccgacaa ccgaggacac ggccacctat    660
ttctgtgcca gaaatggcta tactactggc tggggtgggg acttgtgggg cccaggcacc    720
ctggtcactg tctcttca                                                 738
```

<210> SEQ ID NO 7
<211> LENGTH: 348
<212> TYPE: DNA
<213> ORGANISM: Oryctolagus cuniculus f. domesticus

<400> SEQUENCE: 7

```
cagtcggtgg aggagtccgg gggtcgcctg gtaacgcctg ggacacccct gacactcacc      60
tgcacagtct ctggaatcga cctcagtagc tatgcaataa gctgggtccg ccaggctcca     120
gggaaggggc tggaatacat cggatacatt tggaatgctg gtaacaccta ctacgcgagc     180
tgggcaaaag gccgattcac catctccaaa acctcgacca cggtggatct gaaaatcacc     240
agtccgacaa ccgaggacac ggccacctat ttctgtgcca gaggaacatt agggggactac     300
aatggcatgg acccctgggg cccagggacc ctcgtcaccg tctcttca                  348
```

<210> SEQ ID NO 8
<211> LENGTH: 336
<212> TYPE: DNA
<213> ORGANISM: Oryctolagus cuniculus f. domesticus

<400> SEQUENCE: 8

```
gagctcgatc tgacccagac tccatccccc gtgtctgcgg ctgttggagg cacagtcacc      60
atcaattgcc agtccagtca gactatttat gctaacaggc gcttagcctg gtatcaacag     120
aaaccagggc agcctcccaa gctcctgatc tatggtgcat ccactctggc atctggggtc     180
ccatcgcggt tcaaaggcag tggatctggg acacagttca ctctcaccat cagcggcgtg     240
cagtgtgacg atgctgccac ttactactgt gcaggctata aagttatga tggtgatgat     300
gttggtttcg gcggagggac cgaggtggtc gtcaaa                               336
```

<210> SEQ ID NO 9
<211> LENGTH: 972
<212> TYPE: DNA
<213> ORGANISM: Oryctolagus cuniculus f. domesticus

<400> SEQUENCE: 9

```
ggtcaaccta aggctccgtc agtcttccca ctggcccccct gctgcgggga cacacccagc      60
tccacggtga ccctgggctg cctggtcaaa ggctacctcc cggagccagt gaccgtgacc     120
tggaactcgg gcaccctcac caatggggta cgcaccttcc cgtccgtccg gcagtcctca     180
ggcctctact cgctgagcag cgtggtgagc gtgacctcaa gcagccagcc cgtcacctgc     240
aacgtggccc acccagccac caacaccaaa gtggacaaga ccgttgcgcc ctcgacatgc     300
agcaagccca gtgcccaccc cctgaactc ctgggggggac cgtctgtctt catcttcccc     360
ccaaaaccca aggacaccct catgatctca cgcaccccccg aggtcacatg cgtggtggtg     420
gacgtgagcc aggatgaccc cgaggtgcag ttcacatggt acataaacaa cgagcaggtg     480
cgcaccgccc ggccgccgct acgggagcag cagttcaaca gcacgatccg cgtggtcagc     540
accctcccca tcgcgcacca ggactggctg aggggcaagg agttcaagtg caaagtccac     600
aacaaggcac tcccggcccc catcgagaaa accatctcca agccagagg gcagccctg     660
gagccgaagg tctacaccat gggccctccc cggaggagc tgagcagcag gtcggtcagc     720
ctgacctgca tgatcaacgg cttctaccct tccgacatct cggtggagtg ggagaagaac     780
gggaaggcag aggacaacta caagaccacg ccggccgtgc tggacagcga cggctcctac     840
ttcctctaca gcaagctctc agtgcccacg agtgagtggc agcgggggcga cgtcttcacc     900
tgctccgtga tgcacgaggc cttgcacaac cactacacgc agaagtccat ctcccgctct     960
ccgggtaaat aa                                                         972
```

<210> SEQ ID NO 10
<211> LENGTH: 315

```
<212> TYPE: DNA
<213> ORGANISM: Oryctolagus cuniculus f. domesticus

<400> SEQUENCE: 10
ggggatccag ttgcacctac tgtcctcatc ttcccaccag ctgctgatca ggtggcaact    60
ggaacagtca ccatcgtgtg tgtggcgaat aaatactttc ccgatgtcac cgtcacctgg   120
gaggtggatg gcaccaccca aacaactggc atcgagaaca gtaaacaccg cagaattct    180 gcagattgta cctacaacct cagcagcact ctgacactga ccagcacaca gtacaacagc   240
cacaaagagt acacctgcaa ggtgacccag ggcacgacct cagtcgtcca gagcttcaat   300
aggggtgact gttaa                                                    315

<210> SEQ ID NO 11
<211> LENGTH: 116
<212> TYPE: PRT
<213> ORGANISM: Oryctolagus cuniculus f. domesticus

<400> SEQUENCE: 11

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Ile Ser Trp Val Arg Gln Ala Pro Gly Lys Gly Leu Glu Tyr Ile Gly
        35                  40                  45

Tyr Ile Trp Asn Ala Gly Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Thr
                85                  90                  95

Leu Gly Asp Tyr Asn Gly Met Asp Pro Trp Gly Pro Gly Thr Leu Val
            100                 105                 110

Thr Val Ser Ser
        115

<210> SEQ ID NO 12
<211> LENGTH: 112
<212> TYPE: PRT
<213> ORGANISM: Oryctolagus cuniculus f. domesticus

<400> SEQUENCE: 12

Glu Leu Asp Leu Thr Gln Thr Pro Ser Pro Val Ser Ala Ala Val Gly
1               5                   10                  15

Gly Thr Val Thr Ile Asn Cys Gln Ser Ser Gln Thr Ile Tyr Ala Asn
            20                  25                  30

Arg Arg Leu Ala Trp Tyr Gln Gln Lys Pro Gly Gln Pro Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Tyr Lys Ser Tyr
                85                  90                  95

Asp Gly Asp Asp Val Gly Phe Gly Gly Gly Thr Glu Val Val Val Lys
            100                 105                 110
```

<210> SEQ ID NO 13
<211> LENGTH: 13
<212> TYPE: PRT
<213> ORGANISM: Oryctolagus cuniculus f. domesticus

<400> SEQUENCE: 13

Gln Ser Ser Gln Thr Ile Tyr Ala Asn Arg Arg Leu Ala
1               5                   10

<210> SEQ ID NO 14
<211> LENGTH: 7
<212> TYPE: PRT
<213> ORGANISM: Oryctolagus cuniculus f. domesticus

<400> SEQUENCE: 14

Gly Ala Ser Thr Leu Ala Ser
1               5

<210> SEQ ID NO 15
<211> LENGTH: 12
<212> TYPE: PRT
<213> ORGANISM: Oryctolagus cuniculus f. domesticus

<400> SEQUENCE: 15

Ala Gly Tyr Lys Ser Tyr Asp Gly Asp Asp Val Gly
1               5                   10

<210> SEQ ID NO 16
<211> LENGTH: 10
<212> TYPE: PRT
<213> ORGANISM: Oryctolagus cuniculus f. domesticus

<400> SEQUENCE: 16

Gly Ile Asp Leu Ser Ser Tyr Ala Ile Ser
1               5                   10

<210> SEQ ID NO 17
<211> LENGTH: 16
<212> TYPE: PRT
<213> ORGANISM: Oryctolagus cuniculus f. domesticus

<400> SEQUENCE: 17

Tyr Ile Trp Asn Ala Gly Asn Thr Tyr Tyr Ala Ser Trp Ala Lys Gly
1               5                   10                  15

<210> SEQ ID NO 18
<211> LENGTH: 13
<212> TYPE: PRT
<213> ORGANISM: Oryctolagus cuniculus f. domesticus

<400> SEQUENCE: 18

Ala Arg Gly Thr Leu Gly Asp Tyr Asn Gly Met Asp Pro
1               5                   10

<210> SEQ ID NO 19
<211> LENGTH: 1404
<212> TYPE: DNA
<213> ORGANISM: Artificial sequence
<220> FEATURE:
<223> OTHER INFORMATION: Nucleotide sequence of the humanized antibody
      VEGF165-H988-10 heavy chain containing signal peptide

<400> SEQUENCE: 19
atgggctggt ccctgattct gctgttcctg gtggctgtgg ctaccagggt gctgagtcag     60
tctgtccagg agtctggacc tggactggtg aagccatctg agaccctgtc cctgacttgt    120

```
actgtgtctg gcattgacct gtcctcctat gccatctcct gggtgagaca acctcctggc      180
aagggattgg aatacattgg ctacatctgg aatgctggca acacctacta tgcctcctgg      240
gctaagggca gggtgaccat ctctgtggac accagcaaga accaggtgga cctgaaactg      300
tcctctgtga cagcagcaga cacagcagtc tacttctgtg ccaggggcac cctgggagac      360
tacaatggga tggacccatg gggacctggc accctggtga cagtgtccag cgctagcacc      420
aagggcccat cggtcttccc cctggcaccc tcctccaaga gcacctctgg gggcacagcg      480
gccctgggct gcctggtcaa ggactacttc cccgaaccgg tgacggtgtc gtggaactca      540
ggcgccctga ccagcggcgt gcacaccttc ccggctgtcc tacagtcctc aggactctac      600
tccctcagca gcgtggtgac cgtgccctcc agcagcttgg gcacccagac ctacatctgc      660
aacgtgaatc acaagcccag caacaccaag gtggacaaga agttgagcc caaatcttgt       720 gacaaaactc acacatgccc accgtgccca gcacctgaac tcctgggggg accgtcagtc      780
ttcctcttcc cccaaaaacc caaggacacc ctcatgatct cccggacccc tgaggtcacg      840
tgcgtggtgg tggacgtgag ccacgaagac cccgaggtca agttcaactg gtacgtggac      900
ggcgtggagg tgcataatgc caagacaaag ccgcgggagg agcagtacaa cagcacgtac      960
cgtgtggtca gcgtcctcac cgtcctgcac caggactggc tgaatggcaa ggagtacaag     1020
tgcaaggtct ccaacaaagc cctcccagcc cccatcgaga aaaccatctc caaagccaaa     1080
gggcagcccc gagaaccaca ggtgtacacc ctgcccccat cccgggatga gctgaccaag     1140
aaccaggtca gcctgacctg cctggtcaaa ggcttctatc cagcgacat cgccgtggag      1200 tgggagagca atgggcagcc ggagaacaac tacaagacca cgcctcccgt gctggactcc     1260
gacggctcct tcttcctcta cagcaagctc accgtggaca agagcaggtg gcagcagggg     1320
aacgtcttct catgctccgt gatgcatgag gctctgcaca accactacac gcagaagagc     1380
ctctccctgt ctccgggtaa atga                                            1404
```

<210> SEQ ID NO 20
<211> LENGTH: 717
<212> TYPE: DNA
<213> ORGANISM: Artificial sequence
<220> FEATURE:
<223> OTHER INFORMATION: Nucleotide sequence of humanized antibody
      VEGF165-H988-10 light chain containing signal peptide

<400> SEQUENCE: 20

```
atgggctggt cctgtatcat cctgttcctg gtggctacag ccacaggagt gcatagtgaa       60
ctccaactta cccagagccc atcctccctg tctgcctctg tgggagacag ggtgaccatc      120
acttgtcagt ccagccagac catctatgcc aacaggagac tggcttggta tcaacagaag      180
cctggcaagg tgccaaaact gctgatttat ggagccagca cctggcatc tggagtgcca      240 agcaggttca gggctctgg ctctggcaca gacttcaccc tgaccatctc ctccctccaa      300
cctgaggatg tggctaccta ctactgtgct ggctacaagt cctatgatgg agatgatgtg      360
ggctttggag gaggcaccaa ggtggagatt aagcgtacgg tggctgcacc atctgtcttc     420
atcttcccgc catctgatga gcagttgaaa tctggaactg cctctgttgt gtgcctgctg      480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca aagtctacgc ctgcgaagtc     660
acccatcagg gcctgagctc gcccgtcaca aagagcttca cagggggaga gtgttag        717
```

<210> SEQ ID NO 21
<211> LENGTH: 467
<212> TYPE: PRT
<213> ORGANISM: Artificial sequence
<220> FEATURE:
<223> OTHER INFORMATION: Amino acid sequence of the heavy chain of humanized antibody VEGF165-H988-10 containing signal peptide

<400> SEQUENCE: 21

```
Met Gly Trp Ser Leu Ile Leu Leu Phe Leu Val Ala Val Ala Thr Arg
1               5                   10                  15

Val Leu Ser Gln Ser Val Gln Glu Ser Gly Pro Gly Leu Val Lys Pro
            20                  25                  30

Ser Glu Thr Leu Ser Leu Thr Cys Thr Val Ser Gly Ile Asp Leu Ser
        35                  40                  45

Ser Tyr Ala Ile Ser Trp Val Arg Gln Pro Pro Gly Lys Gly Leu Glu
    50                  55                  60

Tyr Ile Gly Tyr Ile Trp Asn Ala Gly Asn Thr Tyr Tyr Ala Ser Trp
65                  70                  75                  80

Ala Lys Gly Arg Val Thr Ile Ser Val Asp Thr Ser Lys Asn Gln Val
                85                  90                  95

Asp Leu Lys Leu Ser Ser Val Thr Ala Ala Asp Thr Ala Val Tyr Phe
            100                 105                 110

Cys Ala Arg Gly Thr Leu Gly Asp Tyr Asn Gly Met Asp Pro Trp Gly
        115                 120                 125

Pro Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
```

```
              355                 360                 365
Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                    405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 22
<211> LENGTH: 238
<212> TYPE: PRT
<213> ORGANISM: Artificial sequence
<220> FEATURE:
<223> OTHER INFORMATION: Amino acid sequence of the light chain of
      humanized antibody VEGF165-H988-10 containing signal peptide

<400> SEQUENCE: 22

Met Gly Trp Ser Cys Ile Ile Leu Phe Leu Val Ala Thr Ala Thr Gly
1               5                   10                  15

Val His Ser Glu Leu Gln Leu Thr Gln Ser Pro Ser Ser Leu Ser Ala
                20                  25                  30

Ser Val Gly Asp Arg Val Thr Ile Thr Cys Gln Ser Ser Gln Thr Ile
            35                  40                  45

Tyr Ala Asn Arg Arg Leu Ala Trp Tyr Gln Gln Lys Pro Gly Lys Val
        50                  55                  60

Pro Lys Leu Leu Ile Tyr Gly Ala Ser Thr Leu Ala Ser Gly Val Pro
65                  70                  75                  80

Ser Arg Phe Lys Gly Ser Gly Ser Gly Thr Asp Phe Thr Leu Thr Ile
                85                  90                  95

Ser Ser Leu Gln Pro Glu Asp Val Ala Thr Tyr Tyr Cys Ala Gly Tyr
                100                 105                 110

Lys Ser Tyr Asp Gly Asp Val Gly Phe Gly Gly Gly Thr Lys Val
                115                 120                 125

Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 23
<211> LENGTH: 354
<212> TYPE: DNA
<213> ORGANISM: Artificial sequence
<220> FEATURE:
<223> OTHER INFORMATION: Nucleotide sequence of the heavy chain variable
      region of humanized antibody VEGF165-H988-10

<400> SEQUENCE: 23

```
cagtctgtcc aggagtctgg acctggactg gtgaagccat ctgagaccct gtccctgact    60
tgtactgtgt ctggcattga cctgtcctcc tatgccatct cctgggtgag acaacctcct   120
ggcaagggat tggaatacat tggctacatc tggaatgctg gcaacaccta ctatgcctcc   180
tgggctaagg gcagggtgac catctctgtg gacaccagca agaaccaggt ggacctgaaa   240
ctgtcctctg tgacagcagc agacacagca gtctacttct gtgccagggg caccctggga   300
gactacaatg gcatggaccc atggggacct ggcaccctgg tgacagtgtc cagc         354
```

<210> SEQ ID NO 24
<211> LENGTH: 336
<212> TYPE: DNA
<213> ORGANISM: Artificial sequence
<220> FEATURE:
<223> OTHER INFORMATION: Nucleotide sequence of the light chain variable
      region of humanized antibody VEGF165-H988-10

<400> SEQUENCE: 24

```
gaactccaac ttacccagag cccatcctcc ctgtctgcct ctgtgggaga cagggtgacc    60
atcacttgtc agtccagcca gaccatctat gccaacagga gactggcttg gtatcaacag   120
aagcctggca aggtgccaaa actgctgatt tatggagcca gcaccctggc atctggagtg   180
ccaagcaggt tcaagggctc tggctctggc acagacttca ccctgaccat ctcctccctc   240
caacctgagg atgtggctac ctactactgt gctggctaca gtcctatga tggagatgat   300 gtgggctttg gaggaggcac caaggtggag attaag                             336
```

<210> SEQ ID NO 25
<211> LENGTH: 118
<212> TYPE: PRT
<213> ORGANISM: Artificial sequence
<220> FEATURE:
<223> OTHER INFORMATION: Amino acid sequence of the heavy chain variable
      region of antibody VEGF165-H988-10

<400> SEQUENCE: 25

```
Gln Ser Val Gln Glu Ser Gly Pro Gly Leu Val Lys Pro Ser Glu Thr
1               5                   10                  15

Leu Ser Leu Thr Cys Thr Val Ser Gly Ile Asp Leu Ser Ser Tyr Ala
            20                  25                  30

Ile Ser Trp Val Arg Gln Pro Pro Gly Lys Gly Leu Glu Tyr Ile Gly
        35                  40                  45

Tyr Ile Trp Asn Ala Gly Asn Thr Tyr Tyr Ala Ser Trp Ala Lys Gly
    50                  55                  60

Arg Val Thr Ile Ser Val Asp Thr Ser Lys Asn Gln Val Asp Leu Lys
65                  70                  75                  80

Leu Ser Ser Val Thr Ala Ala Asp Thr Ala Val Tyr Phe Cys Ala Arg
                85                  90                  95

Gly Thr Leu Gly Asp Tyr Asn Gly Met Asp Pro Trp Gly Pro Gly Thr
            100                 105                 110

Leu Val Thr Val Ser Ser
```

-continued

115

<210> SEQ ID NO 26
<211> LENGTH: 112
<212> TYPE: PRT
<213> ORGANISM: Artificial sequence
<220> FEATURE:
<223> OTHER INFORMATION: Amino acid sequence of the light chain variable
      region of antibody VEGF165-H988-10

<400> SEQUENCE: 26

Glu Leu Gln Leu Thr Gln Ser Pro Ser Ser Leu Ser Ala Ser Val Gly
1               5                   10                  15

Asp Arg Val Thr Ile Thr Cys Gln Ser Ser Gln Thr Ile Tyr Ala Asn
            20                  25                  30

Arg Arg Leu Ala Trp Tyr Gln Gln Lys Pro Gly Lys Val Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Tyr Lys Ser Tyr
                85                  90                  95

Asp Gly Asp Val Gly Phe Gly Gly Gly Thr Lys Val Glu Ile Lys
            100                 105                 110

<210> SEQ ID NO 27
<211> LENGTH: 13
<212> TYPE: PRT
<213> ORGANISM: Oryctolagus cuniculus f. domesticus

<400> SEQUENCE: 27

Gln Ser Ser Lys Phe Leu Trp Gln Gly Arg Arg Leu Ala
1               5                   10

<210> SEQ ID NO 28
<211> LENGTH: 7
<212> TYPE: PRT
<213> ORGANISM: Oryctolagus cuniculus f. domesticus

<400> SEQUENCE: 28

Gly Ala Ser Thr Leu Ala Ser
1               5

<210> SEQ ID NO 29
<211> LENGTH: 12
<212> TYPE: PRT
<213> ORGANISM: Oryctolagus cuniculus f. domesticus

<400> SEQUENCE: 29

Ala Gly Tyr Lys Ser Tyr Asp Gly Asp Val Val Gly
1               5                   10

<210> SEQ ID NO 30
<211> LENGTH: 10
<212> TYPE: PRT
<213> ORGANISM: Oryctolagus cuniculus f. domesticus

<400> SEQUENCE: 30

Gly Ile Asp Leu Ser Ser Tyr Ala Ile Ser
1               5                   10

```
<210> SEQ ID NO 31
<211> LENGTH: 16
<212> TYPE: PRT
<213> ORGANISM: Oryctolagus cuniculus f. domesticus

<400> SEQUENCE: 31

Tyr Ile Trp Asn Asp Leu Phe Thr Tyr Tyr Ala Ser Trp Ala Lys Gly
1               5                   10                  15

<210> SEQ ID NO 32
<211> LENGTH: 13
<212> TYPE: PRT
<213> ORGANISM: Oryctolagus cuniculus f. domesticus

<400> SEQUENCE: 32

Ala Arg Gly Thr Leu Gly Asp Tyr Gly Gly Met Asp Pro
1               5                   10

<210> SEQ ID NO 33
<211> LENGTH: 448
<212> TYPE: PRT
<213> ORGANISM: Artificial sequence
<220> FEATURE:
<223> OTHER INFORMATION: Amino acid sequence of the heavy chain of
      humanized antibody VEGF-H988

<400> SEQUENCE: 33

Gln Ser Val Gln Glu Ser Gly Pro Gly Leu Val Lys Pro Ser Glu Thr
1               5                   10                  15

Leu Ser Leu Thr Cys Thr Val Ser Gly Ile Asp Leu Ser Ser Tyr Ala
            20                  25                  30

Ile Ser Trp Val Arg Gln Pro Pro Gly Lys Gly Leu Glu Tyr Ile Gly
        35                  40                  45

Tyr Ile Trp Asn Asp Leu Phe Thr Tyr Tyr Ala Ser Trp Ala Lys Gly
    50                  55                  60

Arg Val Thr Ile Ser Val Asp Thr Ser Lys Asn Gln Val Asp Leu Lys
65                  70                  75                  80

Leu Ser Ser Val Thr Ala Ala Asp Thr Ala Val Tyr Phe Cys Ala Arg
                85                  90                  95

Gly Thr Leu Gly Asp Tyr Gly Gly Met Asp Pro Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 34
<211> LENGTH: 219
<212> TYPE: PRT
<213> ORGANISM: Artificial sequence
<220> FEATURE:
<223> OTHER INFORMATION: Amino acid sequence of the light chain of
      humanized antibody VEGF-H988

<400> SEQUENCE: 34

Glu Leu Gln Leu Thr Gln Ser Pro Ser Ser Leu Ser Ala Ser Val Gly
1               5                   10                  15

Asp Arg Val Thr Ile Thr Cys Gln Ser Ser Lys Phe Leu Trp Gln Gly
            20                  25                  30

Arg Arg Leu Ala Trp Tyr Gln Gln Lys Pro Gly Lys Val Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Tyr Lys Ser Tyr
                85                  90                  95

Asp Gly Asp Val Val Gly Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                165                 170                 175
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 35
<211> LENGTH: 467
<212> TYPE: PRT
<213> ORGANISM: Artificial sequence
<220> FEATURE:
<223> OTHER INFORMATION: Amino acid sequence of the heavy chain of
      humanized antibody VEGF-H988 containing signal peptide

<400> SEQUENCE: 35

Met Gly Trp Ser Leu Ile Leu Leu Phe Leu Val Ala Val Ala Thr Arg
1               5                   10                  15

Val Leu Ser Gln Ser Val Gln Glu Ser Gly Pro Gly Leu Val Lys Pro
            20                  25                  30

Ser Glu Thr Leu Ser Leu Thr Cys Thr Val Ser Gly Ile Asp Leu Ser
        35                  40                  45

Ser Tyr Ala Ile Ser Trp Val Arg Gln Pro Pro Gly Lys Gly Leu Glu
    50                  55                  60

Tyr Ile Gly Tyr Ile Trp Asn Asp Leu Phe Thr Tyr Tyr Ala Ser Trp
65                  70                  75                  80

Ala Lys Gly Arg Val Thr Ile Ser Val Asp Thr Ser Lys Asn Gln Val
                85                  90                  95

Asp Leu Lys Leu Ser Ser Val Thr Ala Ala Asp Thr Ala Val Tyr Phe
            100                 105                 110

Cys Ala Arg Gly Thr Leu Gly Asp Tyr Gly Gly Met Asp Pro Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300
```

```
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 36
<211> LENGTH: 238
<212> TYPE: PRT
<213> ORGANISM: Artificial sequence
<220> FEATURE:
<223> OTHER INFORMATION: Amino acid sequence of the light chain of
      humanized antibody VEGF-H988 containing signal peptide

<400> SEQUENCE: 36

Met Gly Trp Ser Cys Ile Ile Leu Phe Leu Val Ala Thr Ala Thr Gly
1               5                   10                  15

Val His Ser Glu Leu Gln Leu Thr Gln Ser Pro Ser Ser Leu Ser Ala
            20                  25                  30

Ser Val Gly Asp Arg Val Thr Ile Thr Cys Gln Ser Ser Lys Phe Leu
        35                  40                  45

Trp Gln Gly Arg Arg Leu Ala Trp Tyr Gln Gln Lys Pro Gly Lys Val
    50                  55                  60

Pro Lys Leu Leu Ile Tyr Gly Ala Ser Thr Leu Ala Ser Gly Val Pro
65                  70                  75                  80

Ser Arg Phe Lys Gly Ser Gly Ser Gly Thr Asp Phe Thr Leu Thr Ile
            85                  90                  95

Ser Ser Leu Gln Pro Glu Asp Val Ala Thr Tyr Tyr Cys Ala Gly Tyr
        100                 105                 110

Lys Ser Tyr Asp Gly Asp Val Val Gly Phe Gly Gly Gly Thr Lys Val
    115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
            165                 170                 175

Ala Leu Gln Ser Gly Asn Ser Gln Glu Ser Val Thr Glu Gln Asp Ser
        180                 185                 190
```

```
Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 37
<211> LENGTH: 19
<212> TYPE: PRT
<213> ORGANISM: Artificial sequence
<220> FEATURE:
<223> OTHER INFORMATION: Amino acid sequence of heavy chain signal
      peptide

<400> SEQUENCE: 37

Met Gly Trp Ser Leu Ile Leu Leu Phe Leu Val Ala Val Ala Thr Arg
1               5                   10                  15

Val Leu Ser

<210> SEQ ID NO 38
<211> LENGTH: 19
<212> TYPE: PRT
<213> ORGANISM: Artificial sequence
<220> FEATURE:
<223> OTHER INFORMATION: Amino acid sequence of light chain signal
      peptide

<400> SEQUENCE: 38

Met Gly Trp Ser Cys Ile Ile Leu Phe Leu Val Ala Thr Ala Thr Gly
1               5                   10                  15

Val His Ser

<210> SEQ ID NO 39
<211> LENGTH: 118
<212> TYPE: PRT
<213> ORGANISM: Artificial sequence
<220> FEATURE:
<223> OTHER INFORMATION: Amino acid sequence of the heavy chain variable
      region of humanized antibody VEGF-H988

<400> SEQUENCE: 39

Gln Ser Val Gln Glu Ser Gly Pro Gly Leu Val Lys Pro Ser Glu Thr
1               5                   10                  15

Leu Ser Leu Thr Cys Thr Val Ser Gly Ile Asp Leu Ser Ser Tyr Ala
            20                  25                  30

Ile Ser Trp Val Arg Gln Pro Pro Gly Lys Gly Leu Glu Tyr Ile Gly
        35                  40                  45

Tyr Ile Trp Asn Asp Leu Phe Thr Tyr Tyr Ala Ser Trp Ala Lys Gly
    50                  55                  60

Arg Val Thr Ile Ser Val Asp Thr Ser Lys Asn Gln Val Asp Leu Lys
65                  70                  75                  80

Leu Ser Ser Val Thr Ala Ala Asp Thr Ala Val Tyr Phe Cys Ala Arg
                85                  90                  95

Gly Thr Leu Gly Asp Tyr Gly Gly Met Asp Pro Trp Gly Gln Gly Thr
            100                 105                 110

Leu Val Thr Val Ser Ser
        115

<210> SEQ ID NO 40
```

<211> LENGTH: 112
<212> TYPE: PRT
<213> ORGANISM: Artificial sequence
<220> FEATURE:
<223> OTHER INFORMATION: Amino acid sequence of the light chain variable
      region of humanized antibody VEGF-H988

<400> SEQUENCE: 40

Glu Leu Gln Leu Thr Gln Ser Pro Ser Ser Leu Ser Ala Ser Val Gly
1               5                   10                  15

Asp Arg Val Thr Ile Thr Cys Gln Ser Ser Lys Phe Leu Trp Gln Gly
                20                  25                  30

Arg Arg Leu Ala Trp Tyr Gln Gln Lys Pro Gly Lys Val Pro Lys Leu
            35                  40                  45

Leu Ile Tyr Gly Ala Ser Thr Leu Ala Ser Gly Val Pro Ser Arg Phe
50                  55                  60

Lys Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Tyr Lys Ser Tyr
                85                  90                  95

Asp Gly Asp Val Val Gly Phe Gly Gly Gly Thr Lys Val Glu Ile Lys
            100                 105                 110

<210> SEQ ID NO 41
<211> LENGTH: 330
<212> TYPE: PRT
<213> ORGANISM: Homo sapiens

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 42
<211> LENGTH: 107
<212> TYPE: PRT
<213> ORGANISM: Homo sapiens

<400> SEQUENCE: 42

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 43
<211> LENGTH: 1404
<212> TYPE: DNA
<213> ORGANISM: Artificial sequence
<220> FEATURE:
<223> OTHER INFORMATION: Nucleotide sequence of humanized antibody
    VEGF-H988 heavy chain containing signal peptide

<400> SEQUENCE: 43
atgggctggt ccctgattct gctgttcctg gtggctgtgg ctaccagggt gctgagtcag      60
tctgtccagg agtctggacc tggactggtg aagccatctg agaccctgtc cctgacttgt     120
actgtgtctg gcattgacct gtcctcctat gccatctcct gggtgagaca acctcctggc     180
aagggattgg aatacattgg ctacatctgg aatgatctct caccctacta tgcctcctgg     240
gctaagggca gggtgaccat ctctgtggac accagcaaga accaggtgga cctgaaactg     300
tcctctgtga cagcagcaga cacagcagtc tacttctgtg ccaggggcac cctgggagac     360
tacggcggga tggacccatg gggacagggc accctggtga cagtgtccag cgcaagcacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540

```
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt     720 gacaaaactc acacatgccc accgtgccca gcacctgaac tcctgggggg accgtcagtc    780
ttcctcttcc ccccaaaacc caaggacacc ctcatgatct cccggacccc tgaggtcacg    840
tgcgtggtgg tggacgtgag ccacgaagac cccgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa ataa                                          1404
```

```
<210> SEQ ID NO 44
<211> LENGTH: 717
<212> TYPE: DNA
<213> ORGANISM: Artificial sequence
<220> FEATURE:
<223> OTHER INFORMATION: Nucleotide sequence of humanized antibody
      VEGF-H988 light chain containing signal peptide

<400> SEQUENCE: 44
```

```
atgggctggt cctgtatcat cctgttcctg gtggctacag ccacaggagt gcatagtgaa     60
ctccaactta cccagagccc atcctccctg tctgcctctg tgggagacag ggtgaccatc    120
acttgtcagt ccagcaagtt cctctggcag ggcaggagac tggcttggta tcaacagaag    180
cctggcaagg tgccaaaact gctgatttat ggagccagca ccctggcatc tggagtgcca    240
agcaggttca agggctctgg ctctggcaca gacttcaccc tgaccatctc ctccctccaa    300
cctgaggatg tggctaccta ctactgtgct ggctacaagt cctatgatgg agatgttgtg    360
ggctttggag gaggcaccaa ggtggagatt aagcgtacgg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca aagtctacgc ctgcgaagtc    660
acccatcagg gcctgagctc gcccgtcaca aagagcttca caggggagag tgttaa        717
```

```
<210> SEQ ID NO 45
<211> LENGTH: 57
<212> TYPE: DNA
<213> ORGANISM: Artificial sequence
<220> FEATURE:
<223> OTHER INFORMATION: Nucleotide sequence of heavy chain signal
      peptide

<400> SEQUENCE: 45
```

```
atgggctggt ccctgattct gctgttcctg gtggctgtgg ctaccagggt gctgagt        57
```

<210> SEQ ID NO 46
<211> LENGTH: 57
<212> TYPE: DNA
<213> ORGANISM: Artificial sequence
<220> FEATURE:
<223> OTHER INFORMATION: Nucleotide sequence of light chain signal
      peptide

<400> SEQUENCE: 46
atgggctggt cctgtatcat cctgttcctg gtggctacag ccacaggagt gcatagt        57

<210> SEQ ID NO 47
<211> LENGTH: 354
<212> TYPE: DNA
<213> ORGANISM: Artificial sequence
<220> FEATURE:
<223> OTHER INFORMATION: Nucleotide sequence of the heavy chain variable
      region of humanized antibody VEGF-H988

<400> SEQUENCE: 47
cagtctgtcc aggagtctgg acctggactg gtgaagccat ctgagaccct gtccctgact        60
tgtactgtgt ctggcattga cctgtcctcc tatgccatct cctgggtgag acaacctcct       120
ggcaagggat tggaatacat tggctacatc tggaatgatc tcttcaccta ctatgcctcc       180
tgggctaagg gcagggtgac catctctgtg acaccagca agaaccaggt ggacctgaaa        240
ctgtcctctg tgacagcagc agacacagca gtctacttct gtgccagggg cacccctggga      300 gactacggcg ggatggaccc atggggacag ggcaccctgg tgacagtgtc cagc             354

<210> SEQ ID NO 48
<211> LENGTH: 336
<212> TYPE: DNA
<213> ORGANISM: Artificial sequence
<220> FEATURE:
<223> OTHER INFORMATION: Nucleotide sequence of the light chain variable
      region of humanized antibody VEGF-H988

<400> SEQUENCE: 48
gaactccaac ttacccagag cccatcctcc ctgtctgcct ctgtgggaga cagggtgacc        60
atcacttgtc agtccagcaa gttcctctgg cagggcagga gactggcttg gtatcaacag       120
aagcctggca aggtgccaaa actgctgatt tatggagcca gcaccctggc atctggagtg       180
ccaagcaggt tcaagggctc tggctctggc acagacttca ccctgaccat ctcctccctc       240
caacctgagg atgtggctac ctactactgt gctggctaca gtcctatga tggagatgtt        300 gtgggctttg gaggaggcac caaggtggag attaag                                 336

<210> SEQ ID NO 49
<211> LENGTH: 993
<212> TYPE: DNA
<213> ORGANISM: Homo sapiens

<400> SEQUENCE: 49
gcaagcacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgccctcca gcagcttggg cacccagacc       240
tacatctgca acgtgaatca caagcccagc aacaccaagg tggacaagaa agttgagccc       300
aaatcttgtg acaaaactca cacatgccca ccgtgcccag cacctgaact cctgggggga       360

```
ccgtcagtct tcctcttccc cccaaaaccc aaggacaccc tcatgatctc ccggacccct    420
gaggtcacgt gcgtggtggt ggacgtgagc cacgaagacc ccgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccggatgag     720 ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa taa                                 993

<210> SEQ ID NO 50
<211> LENGTH: 324
<212> TYPE: DNA
<213> ORGANISM: Homo sapiens

<400> SEQUENCE: 50
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttaa                                           324

<210> SEQ ID NO 51
<211> LENGTH: 246
<212> TYPE: PRT
<213> ORGANISM: Artificial sequence
<220> FEATURE:
<223> OTHER INFORMATION: Amino acid sequence of the rabbit antibody scFv
      used in the construction of antibody VEGF165-R988

<400> SEQUENCE: 51

Glu Leu Asp Leu Thr Gln Thr Pro Ser Pro Val Ser Ala Ala Val Gly
1               5                   10                  15

Gly Thr Val Thr Ile Asn Cys Gln Ser Ser Gln Thr Ile Tyr Ala Asn
            20                  25                  30

Arg Arg Leu Ala Trp Tyr Gln Gln Lys Pro Gly Gln Pro Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Tyr Lys Ser Tyr
                85                  90                  95

Asp Gly Asp Val Gly Phe Gly Gly Gly Thr Glu Val Val Val Lys
            100                 105                 110

Ser Ser Gly Gly Gly Gly Ser Gly Gly Gly Gly Gly Ser Ser Arg
        115                 120                 125

Ser Ser Gln Ser Val Glu Glu Ser Gly Gly Arg Leu Val Thr Pro Gly
    130                 135                 140
```

```
Thr Pro Leu Thr Leu Thr Cys Thr Val Ser Gly Ile Asp Leu Ser Ser
145                 150                 155                 160

Tyr Ala Ile Ser Trp Val Arg Gln Ala Pro Gly Lys Gly Leu Glu Tyr
                165                 170                 175

Ile Gly Tyr Ile Trp Asn Ala Gly Asn Thr Tyr Tyr Ala Ser Trp Ala
            180                 185                 190

Lys Gly Arg Phe Thr Ile Ser Lys Thr Ser Thr Thr Val Asp Leu Lys
        195                 200                 205

Ile Thr Ser Pro Thr Thr Glu Asp Thr Ala Thr Tyr Phe Cys Ala Arg
    210                 215                 220

Gly Thr Leu Gly Asp Tyr Asn Gly Met Asp Pro Trp Gly Pro Gly Thr
225                 230                 235                 240

Leu Val Thr Val Ser Ser
                245
```

<210> SEQ ID NO 52
<211> LENGTH: 18
<212> TYPE: PRT
<213> ORGANISM: Artificial sequence
<220> FEATURE:
<223> OTHER INFORMATION: Amino acid sequence of the linker used in the
      construction of the phage antibody library for the linkage of
      rabbit antibody scFv

<400> SEQUENCE: 52

```
Ser Ser Gly Gly Gly Gly Ser Gly Gly Gly Gly Gly Ser Ser Arg
1               5                   10                  15

Ser Ser
```

<210> SEQ ID NO 53
<211> LENGTH: 1377
<212> TYPE: DNA
<213> ORGANISM: Artificial sequence
<220> FEATURE:
<223> OTHER INFORMATION: Nucleotide sequence of rabbit antibody
      VEGF165-R988 heavy chain containing signal peptide

<400> SEQUENCE: 53

```
atgggctggt ccctgattct gctgttcctg gtggctgtgg ctaccagggt gctgagtcag    60
tcggtggagg agtccggggg tcgcctggta acgcctggga cacccctgac actcacctgc   120
acagtctctg gaatcgacct cagtagctat gcaataagct gggtccgcca ggctccaggg   180
aaggggctgg aatacatcgg atacatttgg aatgctggta cacctactac gcgagctgg   240 gcaaaaggcc gattcaccat ctccaaaacc tcgaccacgg tggatctgaa aatcaccagt   300
ccgacaaccg aggacacggc cacctatttc tgtgccagag aacattaggg gactacaat    360 ggcatggacc cctgggggccc agggaccctc gtcaccgtct cttcaggtca acctaaggct   420
ccgtcagtct tcccactggc ccctgctgc ggggacacac ccagctccac ggtgaccctg    480
ggctgcctgg tcaaaggcta cctcccggag ccagtgaccg tgacctggaa ctcgggcacc   540
ctcaccaatg ggtacgcac cttcccgtcc gtcggcagt cctcaggcct ctactcgctg    600
agcagcgtgt gagcgtgac ctcaagcagc cagcccgtca cctgcaacgt ggcccaccca   660
gccaccaaca ccaaagtgga caagaccgtt gcgccctcga catgcagcaa gcccacgtgc   720
ccaccccctg aactcctggg gggaccgtct gtcttcatct tcccccaaa acccaaggac   780 accctcatga tctcacgcac ccccgaggtc acatgcgtgg tggtgacgt gagccaggat   840 gaccccgagg tgcagttcac atggtacata aacaacgagc aggtgcgcac cgcccggccg   900
```

| | |
|---|---|
| ccgctacggg agcagcagtt caacagcacg atccgcgtgg tcagcaccct ccccatcgcg | 960 |
| caccaggact ggctgagggg caaggagttc aagtgcaaag tccacaacaa ggcactcccg | 1020 |
| gcccccatcg agaaaaccat ctccaaagcc agagggcagc ccctggagcc gaaggtctac | 1080 |
| accatgggcc ctccccggga ggagctgagc agcaggtcgg tcagcctgac ctgcatgatc | 1140 |
| aacggcttct acccttccga catctcggtg gagtgggaga agaacgggaa ggcagaggac | 1200 |
| aactacaaga ccacgccggc cgtgctggac agcgacggct cctacttcct ctacagcaag | 1260 |
| ctctcagtgc ccacgagtga gtggcagcgg ggcgacgtct tcacctgctc cgtgatgcac | 1320 |
| gaggccttgc acaaccacta cacgcagaag tccatctccc gctctccggg taaataa | 1377 |

<210> SEQ ID NO 54
<211> LENGTH: 708
<212> TYPE: DNA
<213> ORGANISM: Artificial sequence
<220> FEATURE:
<223> OTHER INFORMATION: Nucleotide sequence of the rabbit antibody
    VEGF165-R988 light chain containing signal peptide

<400> SEQUENCE: 54

| | |
|---|---|
| atgggctggt cctgtatcat cctgttcctg gtggctacag ccacaggagt gcatagtgag | 60 |
| ctcgatctga cccagactcc atcccccgtg tctgcggctg ttggaggcac agtcaccatc | 120 |
| aattgccagt ccagtcagac tatttatgct aacaggcgct tagcctggta tcaacagaaa | 180 |
| ccagggcagc ctcccaagct cctgatctat ggtgcatcca ctctggcatc tggggtccca | 240 |
| tcgcggttca aggcagtgg atctgggaca cagttcactc tcaccatcag cggcgtgcag | 300 |
| tgtgacgatg ctgccactta ctactgtgca ggctataaaa gttatgatgg tgatgatgtt | 360 |
| ggtttcggcg gagggaccga ggtggtcgtc aaagggatc cagttgcacc tactgtcctc | 420 |
| atcttcccac cagctgctga tcaggtggca actggaacag tcaccatcgt gtgtgtggcg | 480 |
| aataaatact ttcccgatgt caccgtcacc tgggaggtgg atggcaccac ccaaacaact | 540 |
| ggcatcgaga acagtaaaac accgcagaat tctgcagatt gtacctacaa cctcagcagc | 600 |
| actctgacac tgaccagcac acagtacaac agccacaaag agtacacctg caaggtgacc | 660 |
| cagggcacga cctcagtcgt ccagagcttc aatagggtg actgttaa | 708 |

<210> SEQ ID NO 55
<211> LENGTH: 458
<212> TYPE: PRT
<213> ORGANISM: Artificial sequence
<220> FEATURE:
<223> OTHER INFORMATION: Amino acid sequence of the rabbit antibody
    VEGF165-R988 heavy chain containing signal peptide

<400> SEQUENCE: 55

Met Gly Trp Ser Leu Ile Leu Leu Phe Leu Val Ala Val Ala Thr Arg
1               5                   10                  15

Val Leu Ser Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Tyr Ala Ile Ser Trp Val Arg Gln Ala Pro Gly Lys Gly Leu Glu
    50                  55                  60

Tyr Ile Gly Tyr Ile Trp Asn Ala Gly Asn Thr Tyr Tyr Ala Ser Trp
65                  70                  75                  80

Ala Lys Gly Arg Phe Thr Ile Ser Lys Thr Ser Thr Thr Val Asp Leu

```
                85                  90                  95
Lys Ile Thr Ser Pro Thr Thr Glu Asp Thr Ala Thr Tyr Phe Cys Ala
                100                 105                 110

Arg Gly Thr Leu Gly Asp Tyr Asn Gly Met Asp Pro Trp Gly Pro Gly
                115                 120                 125

Thr Leu Val Thr Val Ser Ser Gly Gln Pro Lys Ala Pro Ser Val Phe
130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly Thr Leu Thr Asn Gly Val Arg Thr Phe Pro Ser Val Arg
                180                 185                 190

Gln Ser Ser Gly Leu Tyr Ser Leu Ser Ser Val Val Ser Val Thr Ser
                195                 200                 205

Ser Ser Gln Pro Val Thr Cys Asn Val Ala His Pro Ala Thr Asn Thr
210                 215                 220

Lys Val Asp Lys Thr Val Ala Pro Ser Thr Cys Ser Lys Pro Thr Cys
225                 230                 235                 240

Pro Pro Pro Glu Leu Leu Gly Gly Pro Ser Val Phe Ile Phe Pro Pro
                245                 250                 255

Lys Pro Lys Asp Thr Leu Met Ile Ser Arg Thr Pro Glu Val Thr Cys
                260                 265                 270

Val Val Val Asp Val Ser Gln Asp Asp Pro Glu Val Gln Phe Thr Trp
                275                 280                 285

Tyr Ile Asn Asn Glu Gln Val Arg Thr Ala Arg Pro Pro Leu Arg Glu
                290                 295                 300

Gln Gln Phe Asn Ser Thr Ile Arg Val Val Ser Thr Leu Pro Ile Ala
305                 310                 315                 320

His Gln Asp Trp Leu Arg Gly Lys Glu Phe Lys Cys Lys Val His Asn
                325                 330                 335

Lys Ala Leu Pro Ala Pro Ile Glu Lys Thr Ile Ser Lys Ala Arg Gly
                340                 345                 350

Gln Pro Leu Glu Pro Lys Val Tyr Thr Met Gly Pro Pro Arg Glu Glu
                355                 360                 365

Leu Ser Ser Arg Ser Val Ser Leu Thr Cys Met Ile Asn Gly Phe Tyr
                370                 375                 380

Pro Ser Asp Ile Ser Val Glu Trp Glu Lys Asn Gly Lys Ala Glu Asp
385                 390                 395                 400

Asn Tyr Lys Thr Thr Pro Ala Val Leu Asp Ser Asp Gly Ser Tyr Phe
                405                 410                 415

Leu Tyr Ser Lys Leu Ser Val Pro Thr Ser Glu Trp Gln Arg Gly Asp
                420                 425                 430

Val Phe Thr Cys Ser Val Met His Glu Ala Leu His Asn His Tyr Thr
                435                 440                 445

Gln Lys Ser Ile Ser Arg Ser Pro Gly Lys
450                 455

<210> SEQ ID NO 56
<211> LENGTH: 235
<212> TYPE: PRT
<213> ORGANISM: Artificial sequence
<220> FEATURE:
<223> OTHER INFORMATION: Amino acid sequence of the rabbit antibody
      VEGF165-R988 light chain containing signal peptide
```

<400> SEQUENCE: 56

```
Met Gly Trp Ser Cys Ile Ile Leu Phe Leu Val Ala Thr Ala Thr Gly
1               5                   10                  15

Val His Ser Glu Leu Asp Leu Thr Gln Thr Pro Ser Pro Val Ser Ala
            20                  25                  30

Ala Val Gly Gly Thr Val Thr Ile Asn Cys Gln Ser Ser Gln Thr Ile
        35                  40                  45

Tyr Ala Asn Arg Arg Leu Ala Trp Tyr Gln Gln Lys Pro Gly Gln Pro
    50                  55                  60

Pro Lys Leu Leu Ile Tyr Gly Ala Ser Thr Leu Ala Ser Gly Val Pro
65                  70                  75                  80

Ser Arg Phe Lys Gly Ser Gly Ser Gly Thr Gln Phe Thr Leu Thr Ile
                85                  90                  95

Ser Gly Val Gln Cys Asp Asp Ala Ala Thr Tyr Tyr Cys Ala Gly Tyr
            100                 105                 110

Lys Ser Tyr Asp Gly Asp Val Gly Phe Gly Gly Gly Thr Glu Val
        115                 120                 125

Val Val Lys Gly Asp Pro Val Ala Pro Thr Val Leu Ile Phe Pro Pro
130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235
```

<210> SEQ ID NO 57
<211> LENGTH: 323
<212> TYPE: PRT
<213> ORGANISM: Oryctolagus cuniculus f. domesticus

<400> SEQUENCE: 57

```
Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125
```

Ile Ser Arg Thr Pro Glu Val Thr Cys Val Val Asp Val Ser Gln
130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
                180                 185                 190

Lys Glu Phe Lys Cys Lys Val His Asn Lys Ala Leu Pro Ala Pro Ile
            195                 200                 205

Glu Lys Thr Ile Ser Lys Ala Arg Gly Gln Pro Leu Glu Pro Lys Val
210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
                260                 265                 270

Val Leu Asp Ser Asp Gly Ser Tyr Phe Leu Tyr Ser Lys Leu Ser Val
            275                 280                 285

Pro Thr Ser Glu Trp Gln Arg Gly Asp Val Phe Thr Cys Ser Val Met
290                 295                 300

His Glu Ala Leu His Asn His Tyr Thr Gln Lys Ser Ile Ser Arg Ser
305                 310                 315                 320

Pro Gly Lys

<210> SEQ ID NO 58
<211> LENGTH: 104
<212> TYPE: PRT
<213> ORGANISM: Oryctolagus cuniculus f. domesticus

<400> SEQUENCE: 58

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
                20                  25                  30

Phe Pro Asp Val Thr Val Thr Trp Glu Val Asp Gly Thr Thr Gln Thr
            35                  40                  45

Thr Gly Ile Glu Asn Ser Lys Thr Pro Gln Asn Ser Ala Asp Cys Thr
50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100

<210> SEQ ID NO 59
<211> LENGTH: 33
<212> TYPE: DNA
<213> ORGANISM: Artificial sequence
<220> FEATURE:
<223> OTHER INFORMATION: Forward primer F1 for amplifying the heavy
      chain variable region

<400> SEQUENCE: 59
accagggtgc tgagtcagtc ggtggaggag tcc                    33

<210> SEQ ID NO 60
<211> LENGTH: 24
<212> TYPE: DNA
<213> ORGANISM: Artificial sequence
<220> FEATURE:
<223> OTHER INFORMATION: Reverse primer R1 for amplifying the heavy
      chain variable region

<400> SEQUENCE: 60
tgtgaccagg gtacctgggc ccca                              24

<210> SEQ ID NO 61
<211> LENGTH: 35
<212> TYPE: DNA
<213> ORGANISM: Artificial sequence
<220> FEATURE:
<223> OTHER INFORMATION: Forward primer F2 for amplifying the light
      chain variable region

<400> SEQUENCE: 61
acaggagtgc atagtgagct cgatctgacc cagac                  35

<210> SEQ ID NO 62
<211> LENGTH: 35
<212> TYPE: DNA
<213> ORGANISM: Artificial sequence
<220> FEATURE:
<223> OTHER INFORMATION: Reverse primer R2 for amplifying the light
      chain variable region

<400> SEQUENCE: 62
ggtgcaactg gatccccttt gacgaccacc tcggt                  35

<210> SEQ ID NO 63
<211> LENGTH: 50
<212> TYPE: DNA
<213> ORGANISM: Artificial sequence
<220> FEATURE:
<223> OTHER INFORMATION: Forward primer F3 for whole gene synthesis of
      the heavy chain variable region

<400> SEQUENCE: 63
ccacaggagt gcatagtgaa ctccaactta cccagagccc atcctcctg   50

<210> SEQ ID NO 64
<211> LENGTH: 33
<212> TYPE: DNA
<213> ORGANISM: Artificial sequence
<220> FEATURE:
<223> OTHER INFORMATION: Reverse primer R3 for whole gene synthesis of
      the heavy chain variable region

<400> SEQUENCE: 64
cctgtctccc acagaggcag acagggagga tgg                    33

<210> SEQ ID NO 65
<211> LENGTH: 33
<212> TYPE: DNA
<213> ORGANISM: Artificial sequence
<220> FEATURE:
<223> OTHER INFORMATION: Forward primer F4 for whole gene synthesis of
      the heavy chain variable region

<400> SEQUENCE: 65
tctgtgggag acagggtgac catcacttgt cag                    33

<210> SEQ ID NO 66
<211> LENGTH: 33
<212> TYPE: DNA
<213> ORGANISM: Artificial sequence
<220> FEATURE:
<223> OTHER INFORMATION: Reverse primer R4 for whole gene synthesis of
      the heavy chain variable region

<400> SEQUENCE: 66
ggcatagatg gtctggctgg actgacaagt gat                                   33

<210> SEQ ID NO 67
<211> LENGTH: 28
<212> TYPE: DNA
<213> ORGANISM: Artificial sequence
<220> FEATURE:
<223> OTHER INFORMATION: Forward primer F5 for whole gene synthesis of
      the heavy chain variable region

<400> SEQUENCE: 67
cagaccatct atgccaacag gagactgg                                         28

<210> SEQ ID NO 68
<211> LENGTH: 28
<212> TYPE: DNA
<213> ORGANISM: Artificial sequence
<220> FEATURE:
<223> OTHER INFORMATION: Reverse primer R5 for whole gene synthesis of
      the heavy chain variable region

<400> SEQUENCE: 68
ttctgttgat accaagccag tctcctgt                                         28

<210> SEQ ID NO 69
<211> LENGTH: 28
<212> TYPE: DNA
<213> ORGANISM: Artificial sequence
<220> FEATURE:
<223> OTHER INFORMATION: Forward primer F6 for whole gene synthesis of
      the heavy chain variable region

<400> SEQUENCE: 69
ttggtatcaa cagaagcctg gcaaggtg                                         28

<210> SEQ ID NO 70
<211> LENGTH: 28
<212> TYPE: DNA
<213> ORGANISM: Artificial sequence
<220> FEATURE:
<223> OTHER INFORMATION: Reverse primer R6 for whole gene synthesis of
      the heavy chain variable region

<400> SEQUENCE: 70
aaatcagcag ttttggcacc ttgccagg                                         28

<210> SEQ ID NO 71
<211> LENGTH: 28
<212> TYPE: DNA
<213> ORGANISM: Artificial sequence
<220> FEATURE:
<223> OTHER INFORMATION: Forward primer F7 for whole gene synthesis of
      the heavy chain variable region

<400> SEQUENCE: 71
caaaactgct gatttatgga gccagcac                                         28

<210> SEQ ID NO 72
<211> LENGTH: 28
<212> TYPE: DNA
<213> ORGANISM: Artificial sequence
<220> FEATURE:
<223> OTHER INFORMATION: Reverse primer R7 for whole gene synthesis of
      the heavy chain variable region

<400> SEQUENCE: 72
cactccagat gccagggtgc tggctcca                                            28

<210> SEQ ID NO 73
<211> LENGTH: 33
<212> TYPE: DNA
<213> ORGANISM: Artificial sequence
<220> FEATURE:
<223> OTHER INFORMATION: Forward primer F8 for whole gene synthesis of
      the heavy chain variable region

<400> SEQUENCE: 73
ctggcatctg gagtgccaag caggttcaag ggc                                      33

<210> SEQ ID NO 74
<211> LENGTH: 33
<212> TYPE: DNA
<213> ORGANISM: Artificial sequence
<220> FEATURE:
<223> OTHER INFORMATION: Reverse primer R8 for whole gene synthesis of
      the heavy chain variable region

<400> SEQUENCE: 74
gaagtctgtg ccagagccag agcccttgaa cct                                      33

<210> SEQ ID NO 75
<211> LENGTH: 33
<212> TYPE: DNA
<213> ORGANISM: Artificial sequence
<220> FEATURE:
<223> OTHER INFORMATION: Forward primer F9 for whole gene synthesis of
      the heavy chain variable region

<400> SEQUENCE: 75
tctggcacag acttcaccct gaccatctcc tcc                                      33

<210> SEQ ID NO 76
<211> LENGTH: 33
<212> TYPE: DNA
<213> ORGANISM: Artificial sequence
<220> FEATURE:
<223> OTHER INFORMATION: Reverse primer R9 for whole gene synthesis of
      the heavy chain variable region

<400> SEQUENCE: 76
agccacatcc tcaggttgga gggaggagat ggt                                      33

<210> SEQ ID NO 77
<211> LENGTH: 33
<212> TYPE: DNA
<213> ORGANISM: Artificial sequence
<220> FEATURE:
<223> OTHER INFORMATION: Forward primer F10 for whole gene synthesis of
      the heavy chain variable region

<400> SEQUENCE: 77
cctgaggatg tggctaccta ctactgtgct ggc                                      33

<210> SEQ ID NO 78
<211> LENGTH: 33
<212> TYPE: DNA
<213> ORGANISM: Artificial sequence
<220> FEATURE:
<223> OTHER INFORMATION: Reverse primer R10 for whole gene synthesis of
      the heavy chain variable region

<400> SEQUENCE: 78
atctccatca taggacttgt agccagcaca gta                                    33

<210> SEQ ID NO 79
<211> LENGTH: 33
<212> TYPE: DNA
<213> ORGANISM: Artificial sequence
<220> FEATURE:
<223> OTHER INFORMATION: Forward primer F11 for whole gene synthesis of
      the heavy chain variable region

<400> SEQUENCE: 79
tcctatgatg gagatgatgt gggctttgga gga                                    33

<210> SEQ ID NO 80
<211> LENGTH: 50
<212> TYPE: DNA
<213> ORGANISM: Artificial sequence
<220> FEATURE:
<223> OTHER INFORMATION: Reverse primer R11 for whole gene synthesis of
      the heavy chain variable region

<400> SEQUENCE: 80
ggtgcagcca ccgtacgctt aatctccacc ttggtgcctc ctccaaagcc                  50

<210> SEQ ID NO 81
<211> LENGTH: 51
<212> TYPE: DNA
<213> ORGANISM: Artificial sequence
<220> FEATURE:
<223> OTHER INFORMATION: Forward primer F12 for whole gene synthesis of
      the light chain variable region

<400> SEQUENCE: 81
gctaccaggg tgctgagtca gtctgtccag gagtctggac ctggactggt g                51

<210> SEQ ID NO 82
<211> LENGTH: 33
<212> TYPE: DNA
<213> ORGANISM: Artificial sequence
<220> FEATURE:
<223> OTHER INFORMATION: Reverse primer R12 for whole gene synthesis of
      the light chain variable region

<400> SEQUENCE: 82
ggacagggtc tcagatggct tcaccagtcc agg                                    33

<210> SEQ ID NO 83
<211> LENGTH: 33
<212> TYPE: DNA
<213> ORGANISM: Artificial sequence
<220> FEATURE:
<223> OTHER INFORMATION: Forward primer F13 for whole gene synthesis of
      the light chain variable region

<400> SEQUENCE: 83
tctgagaccc tgtccctgac ttgtactgtg tct                                    33

<210> SEQ ID NO 84

```
<210> SEQ ID NO 84
<211> LENGTH: 33
<212> TYPE: DNA
<213> ORGANISM: Artificial sequence
<220> FEATURE:
<223> OTHER INFORMATION: Reverse primer R13 for whole gene synthesis of
      the light chain variable region

<400> SEQUENCE: 84
ataggaggac aggtcaatgc cagacacagt aca                                33

<210> SEQ ID NO 85
<211> LENGTH: 31
<212> TYPE: DNA
<213> ORGANISM: Artificial sequence
<220> FEATURE:
<223> OTHER INFORMATION: Forward primer F14 for whole gene synthesis of
      the light chain variable region

<400> SEQUENCE: 85
gacctgtcct cctatgccat ctcctgggtg a                                  31

<210> SEQ ID NO 86
<211> LENGTH: 31
<212> TYPE: DNA
<213> ORGANISM: Artificial sequence
<220> FEATURE:
<223> OTHER INFORMATION: Reverse primer R14 for whole gene synthesis of
      the light chain variable region

<400> SEQUENCE: 86
cccttgccag gaggttgtct cacccaggag a                                  31

<210> SEQ ID NO 87
<211> LENGTH: 31
<212> TYPE: DNA
<213> ORGANISM: Artificial sequence
<220> FEATURE:
<223> OTHER INFORMATION: Forward primer F15 for whole gene synthesis of
      the light chain variable region

<400> SEQUENCE: 87
acctcctggc aagggattgg aatacattgg c                                  31

<210> SEQ ID NO 88
<211> LENGTH: 31
<212> TYPE: DNA
<213> ORGANISM: Artificial sequence
<220> FEATURE:
<223> OTHER INFORMATION: Reverse primer R15 for whole gene synthesis of
      the light chain variable region

<400> SEQUENCE: 88
tgccagcatt ccagatgtag ccaatgtatt c                                  31

<210> SEQ ID NO 89
<211> LENGTH: 31
<212> TYPE: DNA
<213> ORGANISM: Artificial sequence
<220> FEATURE:
<223> OTHER INFORMATION: Forward primer F16 for whole gene synthesis of
      the light chain variable region

<400> SEQUENCE: 89
tctggaatgc tggcaacacc tactatgcct c                                  31

<210> SEQ ID NO 90
<211> LENGTH: 31
```

<212> TYPE: DNA
<213> ORGANISM: Artificial sequence
<220> FEATURE:
<223> OTHER INFORMATION: Reverse primer R16 for whole gene synthesis of
      the light chain variable region

<400> SEQUENCE: 90
caccctgccc ttagcccagg aggcatagta g                                 31

<210> SEQ ID NO 91
<211> LENGTH: 33
<212> TYPE: DNA
<213> ORGANISM: Artificial sequence
<220> FEATURE:
<223> OTHER INFORMATION: Forward primer F17 for whole gene synthesis of
      the light chain variable region

<400> SEQUENCE: 91
gctaagggca gggtgaccat ctctgtggac acc                               33

<210> SEQ ID NO 92
<211> LENGTH: 33
<212> TYPE: DNA
<213> ORGANISM: Artificial sequence
<220> FEATURE:
<223> OTHER INFORMATION: Reverse primer R17 for whole gene synthesis of
      the light chain variable region

<400> SEQUENCE: 92
caggtccacc tggttcttgc tggtgtccac aga                               33

<210> SEQ ID NO 93
<211> LENGTH: 33
<212> TYPE: DNA
<213> ORGANISM: Artificial sequence
<220> FEATURE:
<223> OTHER INFORMATION: Forward primer F18 for whole gene synthesis of
      the light chain variable region

<400> SEQUENCE: 93
aaccaggtgg acctgaaact gtcctctgtg aca                               33

<210> SEQ ID NO 94
<211> LENGTH: 33
<212> TYPE: DNA
<213> ORGANISM: Artificial sequence
<220> FEATURE:
<223> OTHER INFORMATION: Reverse primer R18 for whole gene synthesis of
      the light chain variable region

<400> SEQUENCE: 94
gtagactgct gtgtctgctg ctgtcacaga gga                               33

<210> SEQ ID NO 95
<211> LENGTH: 33
<212> TYPE: DNA
<213> ORGANISM: Artificial sequence
<220> FEATURE:
<223> OTHER INFORMATION: Forward primer F19 for whole gene synthesis of
      the light chain variable region

<400> SEQUENCE: 95
gacacagcag tctacttctg tgccaggggc acc                               33

<210> SEQ ID NO 96
<211> LENGTH: 33
<212> TYPE: DNA

-continued

```
<213> ORGANISM: Artificial sequence
<220> FEATURE:
<223> OTHER INFORMATION: Reverse primer R19 for whole gene synthesis of
      the light chain variable region

<400> SEQUENCE: 96
catcccattg tagtctccca gggtgccct ggc                                   33

<210> SEQ ID NO 97
<211> LENGTH: 33
<212> TYPE: DNA
<213> ORGANISM: Artificial sequence
<220> FEATURE:
<223> OTHER INFORMATION: Forward primer F20 for whole gene synthesis of
      the light chain variable region

<400> SEQUENCE: 97
gactacaatg ggatggaccc atggggacct ggc                                  33

<210> SEQ ID NO 98
<211> LENGTH: 50
<212> TYPE: DNA
<213> ORGANISM: Artificial sequence
<220> FEATURE:
<223> OTHER INFORMATION: Reverse primer R20 for whole gene synthesis of
      the light chain variable region

<400> SEQUENCE: 98
gggcccttgg tgctagcgct ggacactgtc accagggtgc caggtcccca                50
```

What is claimed are:

1. An isolated anti-VEGF antibody or antigen-binding fragment thereof, comprising
a heavy chain variable region having a heavy chain CDR1 region having the amino acid sequence as set forth in SEQ ID NO: 30 and a heavy chain CDR2 region having the amino acid sequence as set forth in SEQ ID NO: 31 and a heavy chain CDR3 region having the amino acid sequence as set forth in SEQ ID NO: 32; and
a light chain variable region having a light chain CDR1 region having the amino acid sequence as set forth in SEQ ID NO: 27, a light chain CDR2 region having the amino acid sequence as set forth in SEQ ID NO: 28, and a light chain CDR3 region having the amino acid sequence as set forth in SEQ ID NO: 29,
wherein the antigen-binding fragment thereof, is not a Fab fragment.

2. The anti-VEGF antibody or antigen-binding fragment thereof according to claim 1, comprising
the heavy chain variable region having one of an amino acid sequence as set forth in SEQ ID NO: 39 and the amino acid sequences having one of at least 90%, at least 92%, at least 95%, at least 98%, and at least 99% sequence identity to SEQ ID NO: 39; and
the light chain variable region having one of an amino acid sequence as set forth in SEQ ID NO: 40, and the amino acid sequences having one of at least 90%, at least 92%, at least 95%, at least 98%, and at least 99% sequence identity to SEQ ID NO: 40.

3. The anti-VEGF antibody or antigen-binding fragment thereof according to claim 1, comprising:
a light chain constant region having one of an amino acid sequence as set forth in SEQ ID NO: 42 and an amino acid sequence having one of at least 90%, at least 92%, at least 95%, at least 98%, and at least 99% sequence identity to SEQ ID NO: 42; and
a heavy chain constant region that is an IgG1 heavy chain constant region having one of an amino acid sequence as set forth in SEQ ID NO: 41 and an amino acid sequence having one of at least 90%, at least 92%, at least 95%, at least 98%, and at least 99% sequence identity to SEQ ID NO: 41.

4. The anti-VEGF antibody or antigen-binding fragment thereof according to claim 1, wherein said anti-VEGF antibody or antigen-binding fragment thereof is one of a humanized antibody and a chimeric antibody.

5. The anti-VEGF antibody or antigen-binding fragment thereof according to claim 1, wherein said anti-VEGF antibody or antigen-binding fragment thereof is a monoclonal antibody.

6. The anti-VEGF antibody or antigen-binding fragment thereof according to claim 1, wherein said anti-VEGF antibody or antigen-binding fragment thereof is one of an IgG antibody and an IgG1 antibody.

7. The anti-VEGF antibody or antigen-binding fragment thereof according to claim 1, wherein the binding affinity $K_D$ of said anti-VEGF antibody or antigen-binding fragment thereof to the recombinant human VEGF165 protein is one of 1-100 μM, 5-50 μM, and 19.5 μM.

8. The anti-VEGF antibody or antigen-binding fragment thereof according to claim 1, wherein the antigen-binding fragment is one of Fv, Fab', Fab'-SH, F(ab')2, and a single chain antibody molecule wherein the single chain antibody molecule is one of scFv, di-scFv, tri-scFv, diabody, and scFab.

9. An antibody-drug conjugate, comprising:
(a) an anti-VEGF antibody or antigen-binding fragment thereof comprising:

(i) a heavy chain variable region having a heavy chain CDR1 region having the amino acid sequence as set forth in SEQ ID NO: 30 and a heavy chain CDR2 region having the amino acid sequence as set forth in SEQ ID NO: 31 and a heavy chain CDR3 region having the amino acid sequence as set forth in SEQ ID NO: 32; and (ii) a light chain variable region having a light chain CDR1 region having the amino acid sequence as set forth in SEQ ID NO: 27, a light chain CDR2 region having the amino acid sequence as set forth in SEQ ID NO: 28, and a light chain CDR3 region having the amino acid sequence as set forth in SEQ ID NO: 29; and (b) an additional therapeutic agent, wherein the anti-VEGF antibody or antigen-binding fragment thereof is connected with the additional therapeutic agent via a linker.

\* \* \* \* \*

UNITED STATES PATENT AND TRADEMARK OFFICE
CERTIFICATE OF CORRECTION

PATENT NO. : 12,060,416 B2
APPLICATION NO. : 17/579376
DATED : August 13, 2024
INVENTOR(S) : Liangzhi Xie et al.

It is certified that error appears in the above-identified patent and that said Letters Patent is hereby corrected as shown below:

In the Specification

Column 3, Line 14, "In one embodiment, the binding affinity KD of said anti-VEGF antibody or antigen-binding fragment thereof to the recombinant human VEGF165 protein is 1-100 μM, preferably 5-50 μM, and more preferably 19.5 μM" should read --In one embodiment, the binding affinity KD of said anti-VEGF antibody or antigen-binding fragment thereof to the recombinant human VEGF165 protein is 1-100 pM, preferably 5-50 pM, and more preferably 19.5 pM--.

Column 21, Line 38, "The results shown in Table 3 demonstrate that, the binding affinity KD value of VEGF165-H988 to recombinant human VEGF165 protein was 19.5 μM" should read --The results shown in Table 3 demonstrate that, the binding affinity KD value of VEGF165-H988 to recombinant human VEGF165 protein was 19.5 pM--.

In the Claims

Column 92, in Claim 7, Line 1, "The anti-VEGF antibody or antigen-binding fragment thereof according to claim 1, wherein the binding affinity KD of said anti-VEGF antibody or antigen-binding fragment thereof to the recombinant human VEGF165 protein is one of 1-100 μM, 5-50 μM, and 19.5 μM." should read --The anti-VEGF antibody or antigen-binding fragment thereof according to claim 1, wherein the binding affinity KD of said anti-VEGF antibody or antigen-binding fragment thereof to the recombinant human VEGF165 protein is one of 1-100 pM, 5-50 pM, and 19.5 pM.--.

Signed and Sealed this
Seventh Day of January, 2025

Derrick Brent
*Acting Director of the United States Patent and Trademark Office*